US00RE36359E

United States Patent [19]

Ebashi et al.

[11] E Patent Number: Re. 36,359

[45] Reissued Date of Patent: Oct. 26, 1999

[54] LONG CHAIN CARBOXYLIC ACID IMIDE ESTER

[75] Inventors: Iwao Ebashi; Tetsuo Takigawa, both of Kurashiki; Masayasu Inoue, Osaka, all of Japan

[73] Assignee: Kuraray Co., Ltd., Kurashiki, Japan

[21] Appl. No.: 08/850,021

[22] Filed: May 1, 1997

Related U.S. Patent Documents

Reissue of:

[64] Patent No.: 5,414,089
Issued: May 9, 1995
Appl. No.: 08/106,644
Filed: Aug. 16, 1993

U.S. Applications:

[

[62] Division of application No. 07/872,534, Apr. 23, 1992, Pat. No. 5,336,782.

[30] Foreign Application Priority Data

Apr. 24, 1991 [JP] Japan ..... 3-122737

[51] Int. Cl.[6] ..... C07K 1/00; C07K 17/00; C07K 16/00; C07K 14/00; C07D 207/46; C07D 211/94

[52] U.S. Cl. ..... 530/350; 530/410; 546/243; 548/431; 548/435; 548/475; 548/514; 548/542; 548/548

[58] Field of Search ..... 530/410, 350; 546/243; 548/431, 548

[56] References Cited

U.S. PATENT DOCUMENTS

| | | | |
|---|---|---|---|
| 2,041,265 | 5/1936 | Orthner et al. | 530/410 X |
| 2,729,628 | 1/1956 | Mann | 530/410 X |
| 2,794,796 | 6/1957 | Cavanaugh | 530/410 X |
| 2,866,783 | 12/1958 | Bovarnick | 530/410 X |
| 2,872,450 | 2/1959 | Sasse et al. | 548/542 |
| 2,932,589 | 4/1960 | Meyer et al. | 530/410 X |
| 3,685,998 | 8/1972 | Miller | 530/410 X |
| 3,847,893 | 11/1974 | Brandenburg et al. | 530/410 X |
| 4,234,475 | 11/1980 | Sokol | 530/410 X |
| 4,841,023 | 6/1989 | Horowitz | 530/351 |
| 5,336,782 | 8/1994 | Ebashi et al. | 548/542 |
| 5,414,089 | 5/1995 | Ebashi et al. | 546/243 |

FOREIGN PATENT DOCUMENTS

| | | | |
|---|---|---|---|
| 0 243 322 | 10/1987 | European Pat. Off. | 548/542 |
| 0 314 042 | 5/1989 | European Pat. Off. | 548/542 |
| 0401384 | 12/1990 | European Pat. Off. | 548/542 |
| 0 406 416 | 1/1991 | European Pat. Off. | 548/542 |
| 1-316400 | 12/1989 | Japan . | |
| 86/04145 | 7/1986 | WIPO | 548/542 |
| 89/10348 | 11/1989 | WIPO | 548/542 |
| 90/06952 | 6/1990 | WIPO . | |

OTHER PUBLICATIONS

*Chemical Abstracts*, vol. 96, No. 23, Jun. 7, 1982, Abstract No. 198099n.

*Chemical Abstracts*, vol. 110, No. 3, Jan. 30, 1989, Abstract No. 35963h.

*Chemical Abstracts*, vol. 106, No. 3, Jan. 19, 1987, Abstract No. 15373e.

*Chemical Abstracts*, vol. 84, No. 21, May 24, 1976, Abstract No. 15099w.

*Patent Abstracts of Japan*, Abstract of JP3095125, Apr. 19, 1991.

*Tanpakushitsu Haiburido* (*Protein Hybrids*), Chapters 1, 2, 3 and 6, Kyoritsu Shuppan Co., Apr. 1, 1987, pp. 1–87, 138–163.

*Zoku Tanpakushitsu Haiburido* (*Protein Hybrids, a 2nd series*), Chapters 3, 4, and 6, Kyoritsu Shuppan Co., May 20, 1988, pp. 68–103, 132–166.

*SOD No Shinchiken* (*New Findings on SOD*), Nihon Akuseru Shupuringa Co., Dec. 20, 1990, p. 107.

Wong et al, *Agents and Actions*, vol, 10/3 (1980), 231–239.

*Chemical Abstracts*, vol. 114, 1991, Abstract No. 139322x.

*Chemical Abstracts*, vol. 114, 1991, Abstract No. 164770z.

*Chemical Abstracts*, vol. 115, 1991, Abstract No. 154512y.

*Primary Examiner*—Floyd D. Higel

*Attorney, Agent, or Firm*—Burns, Doane, Swecker & Mathis, L.L.P.

[57] ABSTRACT

Provided is a long chain carboxylic acid imide ester (I)

represented by the following general formula (I)

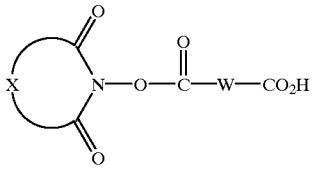

(I)

wherein W is a divalent long chain hydrocarbon group which may optionally be interrupted by one or more groups each independently selected from the group consisting of an oxygen, atom, a sulfur atom, and a group of —N($R^1$)— ($R^1$ being a lower alkyl group) and X represents a divalent hydrocarbon group which may optionally be substituted, or salt thereof. The above long chain carboxylic acid imide ester or its salts is useful for modifying enzymes or proteins having biological activities to give their derivatives which have, while retaining most of the original biological activities, an extremely prolonged plasma half-life as compared with the proteins and have no antigenecities and can be administered to animals.

66 Claims, 6 Drawing Sheets

LONG CHAIN CARBOXYLIC ACID IMIDE ESTER

Matter enclosed in heavy brackets [ ] appears in the original patent but forms no part of this reissue specification; matter printed in italics indicates the additions made by reissue.

This application is a divisional of application Ser. No. 07/872,534, filed Apr. 23, 1992, now U.S. Pat. No. 5,336, 782.

BACKGROUND OF THE INVENTION

1. Field of the Invention

The present invention relates to long chain carboxylic acid imide esters or their salts. The long chain carboxylic acid imide esters or their salts are useful for modifying enzymes or proteins (hereinafter enzymes and proteins are referred to simply as "proteins") having biological activities, to give their derivatives which have, while retaining most of the original biological activities, an extremely prolonged plasma half-life as compared with the proteins and no antigenecities and can be administered to animals.

2. Description of the Prior Art

A number of attempts have been made to improve proteins with various modifiers. Polyethylene glycol (hereinafter referred to as "PEG") is one of those modifiers which have been studied most actively in recent years. PEG is being used for modifying, for example, anticancer agents such as asparaginase, arginase and interleukin-2 (hereinafter referred to as "IL-2"), thrombolytic agents such as urokinase, streptokinase, tissue plasminogen activator (hereinafter referred to as "TPA"), treating agents for enzyme deficiency diseases, such as β-glucosidase, β-glucuronidase, α-galactosidase and adenosine deaminase, gout treating agents such as uricase, anti-inflammatory agents or anti-ischemic agents such as superoxide dismutase (hereinafter sometimes referred to as "SOD"), diabetes treating agent of insulin, and hyperbilirubinemia treating agent or bilirubin oxidase. In more recent years, an attempt was made to modify granulocyte colony-stimulating factor (hereinafter referred to as "G-CSF"), which is one of hematopoietic factors, with PEG to prolong its plasma half-life and to use it for treating hematopoietic disorder and like purposes [Japanese Patent Application Laid-open No. 316400/1989 and International Laid-open No. WO90/06952]. There have been studied and used modifiers other than PEG, and there examples are natural polymers, such as serum albumin and dextran, and polyaspartic acid, partially half-esterified styrene-maleic anhydride copolymer (hereinafter referred to as "SMA") and reactable derivatives of long chain fatty acids ["Tanpakushitsu Haiburido" ("Protein Hybrids"), Chapters 1, 2, 3 and 6, published by Kyoritsu Shuppan Co. on Apr. 1, 1987, "Zoku Tanpakushitsu Haiburido" ("Protein Hybrids; a 2nd series"), Chapters 3, 4 and 6, published by Kyoritsu Shuppan Co. on May 20, 1988 and "SOD No Shinchiken" ("New Findings on SOD"), p. 107, published by Nihon Akuseru Shupuringa Co. on Dec. 20, 1990.]

SOD modified with serum albumin has antigenicity [Agents and Actions, 10, 231 (1980)]. Although the structures of other modifiers including dextran, PEG, polyaspartic acid and SMA can be specified from the viewpoint of polymer chemistry, they have a certain distribution in their molecular weights. The molecular weights of proteins modified with these polymers are therefore not constant, which is a problem in practical applications in view of the current situation in which the compound to be used as a medicinally active ingredient should preferably have a single chemical structure.

Accordingly, an object of the present invention is to provide a novel long chain carboxylic acid imide ester or its salts that can modify proteins to obtain protein derivatives having significantly prolonged plasma half-life as compared with that of unmodified proteins and no antigenicity and can be administered to animals.

This order was well as other objects and advantages of the present invention will be apparent to those skilled in the art from the following detailed description.

SUMMARY OF THE INVENTION

The present invention provides a long chain carboxylic acid imide ester (hereafter referred to as "long chain carboxylic acid imide ester (I)") represented by the following general formula (I)

(I)

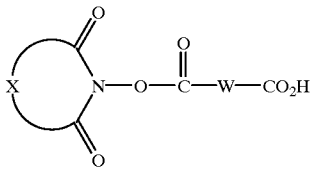

wherein W is a divalent long chain hydrocarbon group which may optionally be interrupted by one or more groups each independently selected from the group consisting of an oxygen atom, a sulfur atom and a group of —N($R^1$)—($R^1$ being a lower alkyl group) and X represents a divalent hydrocarbon residue which may optionally be substituted, or salts thereof.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
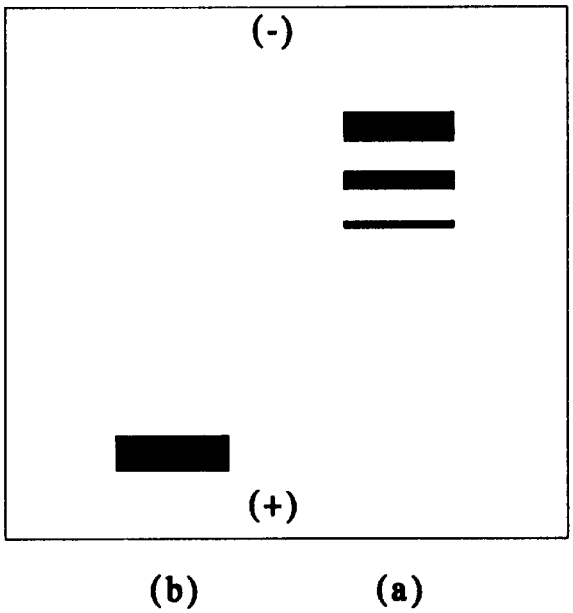
FIG. 1 shows schematic electrophorograms of the reaction mixtures, wherein (a) and (b) are that of the SOD used in Reference Example 1 and that of SOD derivative-C obtained in Reference Example 1, respectively.

The divalent hydrocarbon group represented by W in the long chain carboxylic acid imide ester (I) of the present invention preferably has 8 to 28 principal chain atoms, more preferably 10 to 20 atoms, in view of the usefulness of the long chain carboxylic acid imide ester (I) as chemical modifier for proteins.

Examples of the lower alkyl group represented by $R^1$ are methyl, ethyl, propyl and isopropyl.

Examples of the divalent long chain hydrocarbon group represented by W in the long chain carboxylic acid imide ester (I) are as follows. $(CH_2)_{10}$, $(CH_2)_{11}$, $(CH_2)_{12}$, $(CH_2)_{13}$, $(CH_2)_{14}$, $(CH_2)_{15}$, $(CH_2)_{16}$, $(CH_2)_{17}$, $(CH_2)_{18}$, $(CH_2)_{19}$, $(CH_2)_{20}$, $CH_2CH{=}CH(CH_2)_7$, $(CH_2)_2CH{=}CH(CH_2)_7$, $(CH_2)_3CH{=}CH(CH_2)_7$, $(CH_2)_4CH{=}CH(CH_2)_7$, $(CH_2)_5CH{=}CH(CH_2)_7$, $(CH_2)_6CH{=}CH(CH_2)_7$, $(CH_2)_7CH{=}CH(CH_2)_7$, $(CH_2)_8CH{=}CH(CH_2)_7$, $(CH_2)_9CH{=}CH(CH_2)_7$, $(CH_2)_{10}CH{=}CH(CH_2)_7$, $(CH_2)_{11}CH{=}CH(CH_2)_7$, $(CH_2)_8CH{=}CHCH_2$, $(CH_2)_8CH{=}CH(CH_2)_2$, $(CH_2)_8CH{=}CH(CH_2)_3$, $(CH_2)_8CH{=}CH(CH_2)_4$, $(CH_2)_8CH{=}CH(CH_2)_5$, $(CH_2)_8CH{=}CH(CH_2)_6$, $(CH_2)_8CH{=}CH(CH_2)_7$, $(CH_2)_8CH{=}CH(CH_2)_8$, $(CH_2)_8CH{=}CH(CH_2)_9$, $(CH_2)_8CH{=}CH(CH_2)_{10}$, $CH_2CH{=}CHCH_2CH{=}CH(CH_2)_7$, $(CH_2)_2CH{=}CHCH_2CH{=}CH(CH_2)_7$, $(CH_2)_3CH{=}CHCH_2CH{=}CH(CH_2)_7$, $(CH_2)_4CH{=}CHCH_2CH{=}CH(CH_2)_7$, $(CH_2)_5CH{=}CHCH_2CH{=}CH(CH_2)_7$, $(CH_2)_6CH{=}CHCH_2CH{=}CH(CH_2)_7$, $(CH_2)_7CH{=}CHCH_2CH{=}CH(CH_2)_7$, $(CH_2)_8CH{=}CHCH_2CH{=}CH(CH_2)_7$, $(CH_2)_2{-}O{-}(CH_2)_7$, $(CH_2)_2{-}O{-}(CH_2)_8$, $(CH_2)_2{-}O{-}(CH_2)_9$, $(CH_2)_2{-}O{-}(CH_2)_{10}$, $(CH_2)_2{-}O{-}(CH_2)_{11}$, [$(CH_2)_2{-}O{-}(CH_2)_2$,] $(CH_2)_2{-}O{-}(CH_2)_{12}$, $(CH_2)_2{-}O{-}(CH_2)_{13}$, $(CH_2)_2{-}O{-}(CH_2)_{14}$, $(CH_2)_2{-}O{-}(CH_2)_{15}$, $(CH_2)_2{-}O{-}(CH_2)_{16}$, $(CH_2)_2{-}O{-}(CH_2)_{17}$, $(CH_2)_4{-}O{-}(CH_2)_5$, $(CH_2)_4{-}O{-}(CH_2)_6$, $(CH_2)_4{-}O{-}(CH_2)_7$, $(CH_2)_4{-}O{-}(CH_2)_8$, $(CH_2)_4{-}O{-}(CH_2)_9$, $(CH_2)_4{-}O{-}(CH_2)_{10}$, $(CH_2)_4{-}O{-}(CH_2)_{11}$, $(CH_2)_4{-}O{-}(CH_2)_{12}$, $(CH_2)_4{-}O{-}(CH_2)_{13}$, $(CH_2)_4{-}O{-}(CH_2)_{14}$, $(CH_2)_4{-}O{-}(CH_2)_{15}$, $(CH_2)_6{-}O{-}(CH_2)_3$, $(CH_2)_6{-}O{-}(CH_2)_4$, $(CH_2)_6{-}O{-}(CH_2)_5$, $(CH_2)_6{-}O{-}(CH_2)_6$, $(CH_2)_6{-}O{-}(CH_2)_7$, $(CH_2)_6{-}O{-}(CH_2)_8$, $(CH_2)_6{-}O{-}(CH_2)_9$, $(CH_2)_6{-}O{-}(CH_2)_{10}$, $(CH_2)_6{-}O{-}(CH_2)_{11}$, $(CH_2)_6{-}O{-}(CH_2)_{12}$, $(CH_2)_6{-}O{-}(CH_2)_{13}$, $(CH_2)_8{-}O{-}CH_2$, $(CH_2)_8{-}O{-}(CH_2)_2$, $(CH_2)_8{-}O{-}(CH_2)_3$, $(CH_2)_8{-}O{-}(CH_2)_4$, $(CH_2)_8{-}O{-}(CH_2)_5$, $(CH_2)_8{-}O{-}(CH_2)_6$, $(CH_2)_8{-}O{-}(CH_2)_7$, $(CH_2)_8{-}O{-}(CH_2)_8$, $(CH_2)_8{-}O{-}(CH_2)_9$, $(CH_2)_8{-}O{-}(CH_2)_{10}$, $(CH_2)_8{-}O{-}(CH_2)_{11}$, $(CH_2)_{10}{-}O{-}CH_2$, $(CH_2)_{10}{-}O{-}(CH_2)_2$, $(CH_2)_{10}{-}O{-}(CH_2)_3$, $(CH_2)_{10}{-}O{-}(CH_2)_4$, $(CH_2)_{10}{-}O{-}(CH_2)_5$, $(CH_2)_{10}{-}O{-}(CH_2)_6$, $(CH_2)_{10}{-}O{-}(CH_2)_7$, $(CH_2)_{10}{-}O{-}(CH_2)_8$, $(CH_2)_{10}{-}O{-}(CH_2)_9$, $(CH_2)_{12}{-}O{-}CH_2$, $(CH_2)_{12}{-}O{-}(CH_2)_2$, $(CH_2)_{12}{-}O{-}(CH_2)_3$, $(CH_2)_{12}{-}O{-}(CH_2)_4$, $(CH_2)_{12}{-}O{-}(CH_2)_5$, $(CH_2)_{12}{-}O{-}(CH_2)_6$, $(CH_2)_{12}{-}O{-}(CH_2)_7$, $CH_2{-}O{-}(CH_2)_5CH{=}CH(CH_2)_7$, $(CH_2)_2{-}O{-}(CH_2)_5CH{=}CH(CH_2)_7$, $(CH_2)_3{-}O{-}(CH_2)_5CH{=}CH(CH_2)_7$, $(CH_2)_4{-}O{-}(CH_2)_5CH{=}CH(CH_2)_7$, $(CH_2)_5{-}O{-}(CH_2)_5CH{=}CH(CH_2)_7$, $(CH_2)_2{-}S{-}(CH_2)_7$, $(CH_2)_2{-}S{-}(CH_2)_8$, $(CH_2)_2{-}S{-}(CH_2)_9$, $(CH_2)_2{-}S{-}(CH_2)_{10}$, $(CH_2)_2{-}S{-}(CH_2)_{11}$, $(CH_2)_2{-}S{-}(CH_2)_{12}$, $(CH_2)_2{-}S{-}(CH_2)_{13}$, $(CH_2)_2{-}S{-}(CH_2)_{14}$, $(CH_2)_2{-}S{-}(CH_2)_{15}$, $(CH_2)_2{-}S{-}(CH_2)_{16}$, $(CH_2)_2{-}S{-}(CH_2)_{17}$, $(CH_2)_4{-}S{-}(CH_2)_5$, $(CH_2)_4{-}S{-}(CH_2)_6$, $(CH_2)_4{-}S{-}(CH_2)_7$, $(CH_2)_4{-}S{-}(CH_2)_8$, $(CH_2)_4{-}S{-}(CH_2)_9$, $(CH_2)_4{-}S{-}(CH_2)_{10}$, $(CH_2)_4{-}S{-}(CH_2)_{11}$, $(CH_2)_4{-}S{-}(CH_2)_{12}$, $(CH_2)_4{-}S{-}(CH_2)_{13}$, $(CH_2)_4{-}S{-}(CH_2)_{14}$, $(CH_2)_4{-}S{-}(CH_2)_{15}$, $(CH_2)_6{-}S{-}(CH_2)_3$, $(CH_2)_6{-}S{-}(CH_2)_4$, $(CH_2)_6{-}S{-}(CH_2)_5$, $(CH_2)_6{-}S{-}(CH_2)_6$, $(CH_2)_6{-}S{-}(CH_2)_7$, $(CH_2)_6{-}S{-}(CH_2)_8$, $(CH_2)_6{-}S{-}(CH_2)_9$, $(CH_2)_6{-}S{-}(CH_2)_{10}$, $(CH_2)_6{-}S{-}(CH_2)_{11}$, $(CH_2)_6{-}S{-}(CH_2)_{12}$, $(CH_2)_6{-}S{-}(CH_2)_{13}$, $(CH_2)_8{-}S{-}CH_2$, $(CH_2)_8{-}S{-}(CH_2)_2$, $(CH_2)_8{-}S{-}(CH_2)_3$, $(CH_2)_8{-}S{-}(CH_2)_4$, $(CH_2)_8{-}S{-}(CH_2)_5$, $(CH_2)_8{-}S{-}(CH_2)_6$, $(CH_2)_8{-}S{-}(CH_2)_7$, $(CH_2)_8{-}S{-}(CH_2)_8$, $(CH_2)_8{-}S{-}(CH_2)_9$, $(CH_2)_8{-}S{-}(CH_2)_{10}$, $(CH_2)_8{-}S{-}(CH_2)_{11}$, $(CH_2)_{10}{-}S{-}CH_2$, $(CH_2)_{10}{-}S{-}(CH_2)_2$, $(CH_2)_{10}{-}S{-}(CH_2)_3$, $(CH_2)_{10}{-}S{-}(CH_2)_4$, $(CH_2)_{10}{-}S{-}(CH_2)_5$, $(CH_2)_{10}{-}S{-}(CH_2)_6$, $(CH_2)_{10}{-}S{-}(CH_2)_7$, $(CH_2)_{10}{-}S{-}(CH_2)_8$, $(CH_2)_{10}{-}S{-}(CH_2)_9$, $(CH_2)_{12}{-}S{-}CH_2$, $(CH_2)_{12}{-}S{-}(CH_2)_2$, $(CH_2)_{12}{-}S{-}(CH_2)_3$, $(CH_2)_{12}{-}S{-}(CH_2)_4$, $(CH_2)_{12}{-}S{-}(CH_2)_5$, $(CH_2)_{12}{-}S{-}(CH_2)_6$, $(CH_2)_{12}{-}S{-}(CH_2)_7$, $(CH_2)_2{-}N(CH_3){-}(CH_2)_7$, $(CH_2)_2{-}N(CH_3){-}(CH_2)_8$, $(CH_2)_2{-}N(CH_3){-}(CH_2)_9$, $(CH_2)_2{-}N(CH_3){-}(CH_2)_{10}$, $(CH_2)_2{-}N(CH_3){-}(CH_2)_{11}$, $(CH_2)_2{-}N(CH_3){-}(CH_2)_{12}$, $(CH_2)_2{-}N(CH_3){-}(CH_2)_{13}$, $(CH_2)_2{-}N(CH_3){-}(CH_2)_{14}$, $(CH_2)_2{-}N(CH_3){-}(CH_2)_{15}$, $(CH_2)_2{-}N(CH_3){-}(CH_2)_{16}$, $(CH_2)_2{-}N(CH_3){-}(CH_2)_{17}$, $(CH_2)_4{-}N(CH_3){-}(CH_2)_5$, $(CH_2)_4{-}N(CH_3){-}(CH_2)_6$, $(CH_2)_4{-}N(CH_3){-}(CH_2)_7$, $(CH_2)_4{-}N(CH_3){-}(CH_2)_8$, $(CH_2)_4{-}N(CH_3){-}(CH_2)_9$, $(CH_2)_4{-}N(CH_3){-}(CH_2)_{10}$, $(CH_2)_4{-}N(CH_3){-}(CH_2)_{11}$, $(CH_2)_4{-}N(CH_3){-}(CH_2)_{12}$, $(CH_2)_4{-}N(CH_3){-}(CH_2)_{13}$, $(CH_2)_4{-}N(CH_3){-}(CH_2)_{14}$, $(CH_2)_4{-}N(CH_3){-}(CH_2)_{15}$, $(CH_2)_6{-}N(CH_3){-}(CH_2)_3$, $(CH_2)_6{-}N(CH_3){-}(CH_2)_4$, $(CH_2)_6{-}N(CH_3){-}(CH_2)_5$, $(CH_2)_6{-}N(CH_3){-}(CH_2)_6$, $(CH_2)_6{-}N(CH_3){-}(CH_2)_7$, $(CH_2)_6{-}N(CH_3){-}(CH_2)_8$, $(CH_2)_6{-}N(CH_3){-}(CH_2)_9$, $(CH_2)_6{-}N(CH_3){-}(CH_2)_{10}$, $(CH_2)_6{-}N(CH_3){-}(CH_2)_{11}$, $(CH_2)_6{-}N(CH_3){-}(CH_2)_{12}$, $(CH_2)_6{-}N(CH_3){-}(CH_2)_{13}$, $(CH_2)_2{-}N(C_2H_5){-}(CH_2)_7$, $(CH_2)_2{-}N(C_2H_5){-}(CH_2)_8$, $(CH_2)_2{-}N(C_2H_5){-}(CH_2)_9$, $(CH_2)_2{-}N(C_2H_5){-}(CH_2)_{10}$, $(CH_2)_2{-}N(C_2H_5){-}(CH_2)_{11}$, $(CH_2)_2{-}N(C_2H_5){-}(CH_2)_{12}$, $(CH_2)_2{-}N(C_2H_5){-}(CH_2)_{13}$, $(CH_2)_2{-}N(C_2H_5){-}(CH_2)_{14}$, $(CH_2)_2{-}N(C_2H_5){-}(CH_2)_{15}$, $(CH_2)_2{-}N(C_2H_5){-}(CH_2)_{16}$, $(CH_2)_2{-}N(C_2H_5){-}(CH_2)_{17}$, $(CH_2)_4{-}N(C_2H_5){-}(CH_2)_5$, $(CH_2)_4{-}N(C_2H_5){-}(CH_2)_6$, $(CH_2)_4{-}N(C_2H_5){-}(CH_2)_7$, $(CH_2)_4{-}N(C_2H_5){-}(CH_2)_8$, $(CH_2)_4{-}N(C_2H_5){-}(CH_2)_9$, $(CH_2)_4{-}N(C_2H_5){-}(CH_2)_{10}$, $(CH_2)_4{-}N(C_2H_5){-}(CH_2)_{11}$, $(CH_2)_4{-}N(C_2H_5){-}(CH_2)_{12}$, $(CH_2)_4{-}N(C_2H_5){-}(CH_2)_{13}$, $(CH_2)_4{-}N(C_2H_5){-}(CH_2)_{14}$, $(CH_2)_4{-}N(C_2H_5){-}(CH_2)_{15}$, $(CH_2)_6{-}N(C_2H_5){-}(CH_2)_3$, $(CH_2)_6{-}N(C_2H_5){-}(CH_2)_4$, $(CH_2)_6{-}N(C_2H_5){-}(CH_2)_5$, $(CH_2)_6{-}N(C_2H_5){-}(CH_2)_6$, $(CH_2)_6{-}N(C_2H_5){-}(CH_2)_7$, $(CH_2)_6{-}N(C_2H_5){-}(CH_2)_8$, $(CH_2)_6{-}N(C_2H_5){-}(CH_2)_9$, $(CH_2)_6{-}N(C_2H_5){-}(CH_2)_{10}$, $(CH_2)_6{-}N(C_2H_5){-}(CH_2)_{11}$, $(CH_2)_6{-}N(C_2H_5){-}(CH_2)_{12}$, $(CH_2)_6{-}N(C_2H_5){-}(CH_2)_{13}$, $(CH_2)_2{-}O{-}(CH_2)_2{-}O{-}(CH_2)_4$, $(CH_2)_2{-}O{-}(CH_2)_2{-}O{-}(CH_2)_5$, $(CH_2)_2{-}O{-}(CH_2)_2{-}O{-}(CH_2)_6$, $(CH_2)_2{-}O{-}(CH_2)_2{-}O{-}(CH_2)_7$, $(CH_2)_2{-}O{-}(CH_2)_2{-}O{-}(CH_2)_8$, $(CH_2)_2{-}O{-}(CH_2)_2{-}O{-}(CH_2)_9$, $(CH_2)_2{-}O{-}(CH_2)_2{-}O{-}(CH_2)_{10}$, [$(CH_2)_2{-}o{-}(CH_2)_2{-}O{-}(CH_2)_{11}$,] $(CH_2)_2{-}O{-}(CH_2)_2{-}O{-}(CH_2)_{11}$, $(CH_2)_2{-}O{-}(CH_2)_2{-}O{-}(CH_2)_{12}$, $(CH_2)_2{-}O{-}(CH_2)_2{-}O{-}(CH_2)_{13}$, $(CH_2)_2{-}O{-}(CH_2)_2{-}O{-}(CH_2)_{14}$, $(CH_2)_4{-}O{-}(CH_2)_2{-}O{-}(CH_2)_2$, $(CH_2)_4{-}O{-}(CH_2)_2{-}O{-}(CH_2)_3$, $(CH_2)_4{-}O{-}(CH_2)_2{-}O{-}(CH_2)_4$, $(CH_2)_4{-}O{-}(CH_2)_2{-}O{-}(CH_2)_5$, $(CH_2)_4{-}O{-}(CH_2)_2{-}O{-}(CH_2)_6$, $(CH_2)_4{-}O{-}(CH_2)_2{-}O{-}(CH_2)_7$, $(CH_2)_4{-}O{-}(CH_2)_2{-}O{-}(CH_2)_8$, $(CH_2)_4$—O—$(CH_2)_2$—O—$(CH_2)_9$, $(CH_2)_4$—O—$(CH_2)_2$—O—$(CH_2)_{10}$, $(CH_2)_4$—O—$(CH_2)_2$—O—$(CH_2)_{11}$, $(CH_2)_4$—O—$(CH_2)_2$—O—$(CH_2)_{12}$, $(CH_2)_2$—S—S—$(CH_2)_7$, $(CH_2)_2$—S—S—$(CH_2)_9$, $(CH_2)_2$—S—S—$(CH_2)_{11}$, $(CH_2)_2$—S—S—$(CH_2)_{13}$, $(CH_2)_2$—S—S—$(CH_2)_{15}$, $(CH_2)_4$—S—S—$(CH_2)_5$, $(CH_2)_4$—S—S—$(CH_2)_7$, $(CH_2)_4$—S—S—$(CH_2)_9$, $(CH_2)_4$—S—S—$(CH_2)_{11}$, $(CH_2)_4$—S—S—$(CH_2)_{13}$, $(CH_2)_6$—S—S—$(CH_2)_3$, $(CH_2)_6$—S—S—$(CH_2)_5$, $(CH_2)_6$—S—S—$(CH_2)_7$, $(CH_2)_6$—S—S—$(CH_2)_9$, $(CH_2)_6$—S—S—$(CH_2)_{11}$, $(CH_2)_8$—S—S—$(CH_2$, $(CH_2)_8$—S—S—$(CH_2)_3$, $(CH_2)_8$—S—S—$(CH_2)_5$, $(CH_2)_8$—S—S—$(CH_2)_7$, $(CH_2)_8$—S—S—$(CH_2)_9$.

The imide moiety of the long chain carboxylic acid imide ester (I) may be of any structure in view of the usefulness of the long chain carboxylic acid imide ester (I) as chemical modifiers for proteins. The groups represented by X in the above general formula (I) therefore does not constitute an essential part of the invention and may be any divalent hydrocarbon residue without limitation.

It is however desirable, in view of availability of starting materials and easiness of synthesis, to use as the imide part of the long chain carboxylic acid imide ester (I)

an imide part represented by the following general formula (A) (hereinafter referred to as "imide part A")

(A)

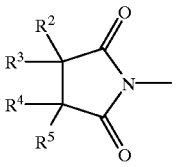

wherein $R^2$, $R^3$, $R^4$ and $R^5$, which may be the same or different, each represents a hydrogen atom, an alkyl group, an aryl groups, an aralkyl group, an —$SO_3H$ group, a group represented by —$OR^6$ wherein $R^6$ represents a hydrogen atom, an alkyl group, an aryl group, an aralkyl group or an acyl group, a group represented by —$NR^7R^8$ wherein $R^7$ and $R^8$, which may be the same or different, each represents an alkyl group, an aryl group, an aralkyl group or an acyl group or a group represented by —$CO_2R^9$ wherein $R^9$ represents a hydrogen atom, an alkyl group, an aryl group or an aralkyl group, $R^2$, $R^3$, $R^4$ and $R^5$ may, in combination with the carbon atoms to which they bond, form a ring which may be substituted, $R^2$ and $R^3$ and/or $R^4$ and $R^5$, in combination, may represent a methylene group which may be substituted; or an imide part represented by the following general formula (B)

(B)

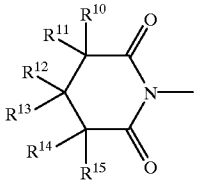

wherein $R^{10}$, $R^{11}$, $R^{12}$, $R^{13}$, $R^{14}$ and $R^{15}$, which may be the same or different, each represents a hydrogen atom, an alkyl group, an aryl group, an aralkyl group, an —$SO_3H$ group, a group represented by the formula —$OR^6$ wherein $R^6$ is as defined above, a group represented by the formula —$NR^7R^8$ wherein $R^7$ and $R^8$ are as defined above or a group represented by the formula —$CO_2R^9$ wherein $R^9$ is as defined above; of which the imide part A is more preferred.

Examples of the alkyl group that may be represented by $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in the above formulas (A) and (B) are methyl, ethyl, propyl, isopropyl and octadecyl. Examples of the aryl group are phenyl and p-bromophenyl. Examples of the aralkyl group are benzyl and p-methoxybenzyl. Examples of the acyl group that may be represented by $R^6$, $R^7$ and $R^8$ are acetyl and benzoyl.

Examples of the group represented by the formula —$OR^6$ are hydroxyl group, alkoxy groups such as methoxy, ethoxy, propoxy and isopropoxy, aryloxy groups such as phenoxy and p-bromophenoxy and aralkyloxy groups such as benzyloxy and p-methoxybenzyloxy. Examples of the group represented by the formula —$NR^7R^8$ are substituted amino groups such as dimethylamino and diethylamino and N-substituted acylamido groups such as N-methylacetamido and N-methylbenzamido. Examples of the group represented by the formula —$CO_2R^9$ are carboxyl group, alkoxycarbonyl groups such as methoxycarbonyl, ethoxycarbonyl, propoxycarboxyl and isopropoxycarbonyl and aryloxycarbonyl groups such as phenoxycarbonyl and p-bromophenoxycarbonyl.

In the above formula (A), where $R^2$, $R^3$, $R^4$ and $R^5$ form, in combination with the carbon atoms to which they bond, a saturated or unsaturated ring which may be substituted, examples of the saturated or unsaturated ring which may be substituted are those having as basic skeleton benzene ring, cyclohexane ring and cyclopentane ring, as well as bicyclo[2,2,1]heptane skeleton, bicyclo[2,2,1] hepta-2-en skeleton, 7-oxabicyclo[2,2,1]heptane skeleton and 7-oxabicyclo[2,2,1]-hepta-2-en skeleton.

Concrete examples of the imide part A having these saturated or unsaturated ring are as follows.

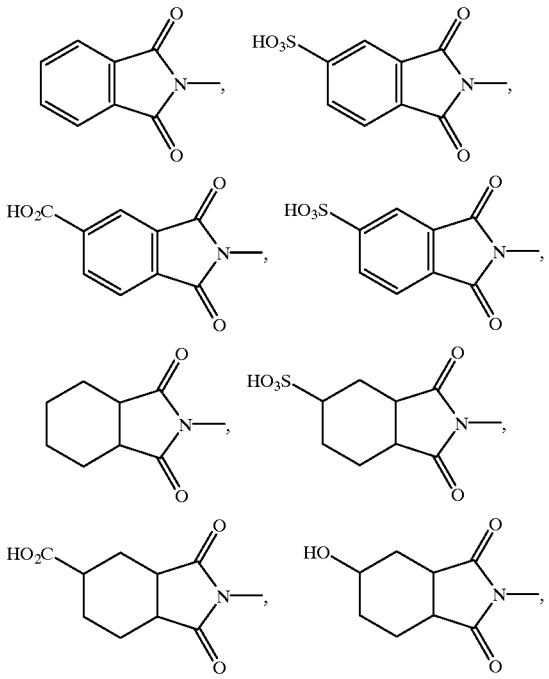

-continued

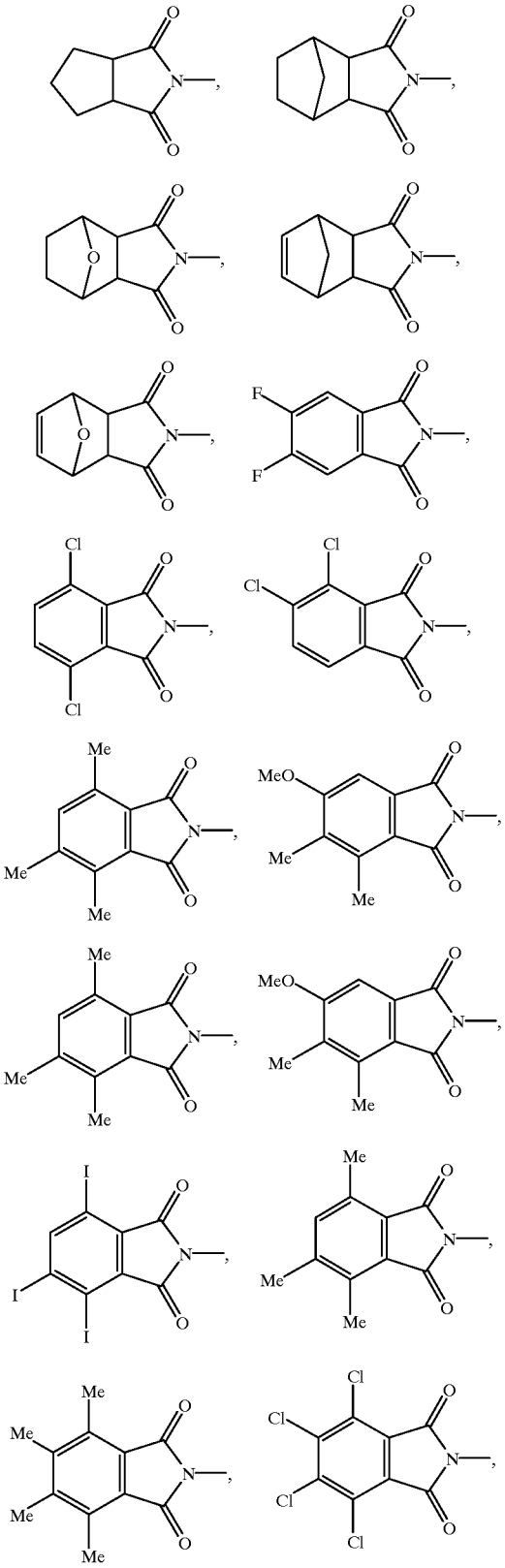

-continued

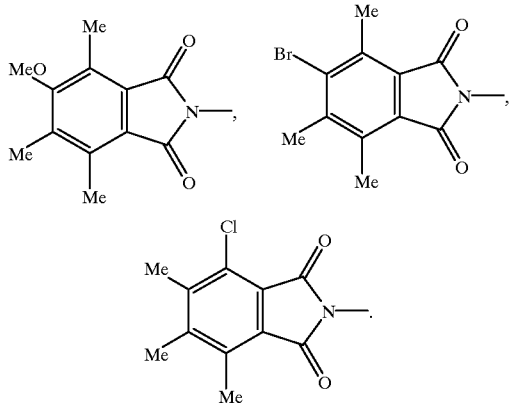

Where $R^2$ and $R^3$ and/or $R^4$ and $R^5$, in combination, each form a methylene group which may be substituted, examples of the methylene group which may be substituted are methylene group and isopropylidene group.

Concrete examples of the imide part A having the methylene group which may be substituted are shown below.

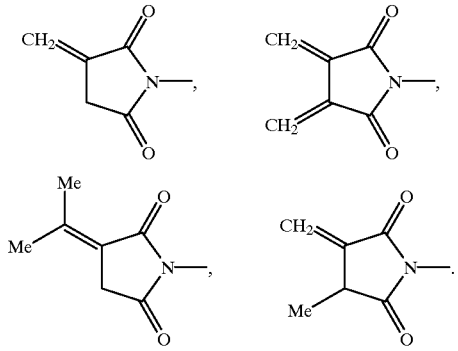

Examples of the salt of the long chain carboxylic acid imide ester (I) are salts with alkali metals, e.g. lithium, sodium and potassium and salts with alkali earth metals, e.g. magnesium and calcium. The salts are formed at the long chain carboxylic acid part and/or imide part of the long chain carboxylic acid imide ester (I).

The long chain carboxylic acid imide ester (I) is produced by subjecting a long chain dicarboxylic acid (hereinafter referred to as "long chain dicarboxylic acid (II)") represented by the general formula (II)

$$HO_2C—W—CO_2H \qquad (II)$$

wherein W is as defined above, to dehydration condensation with an equimolar amount of an N-hydroxyimide (hereinafter referred to as "N-hydroximide (III)") represented by the following general formula (III)).

(III)

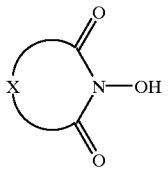

wherein X is as defined before, in the presence of dicyclohexylcarbodiimide (hereinafter referred to as "DCC").

The long chain carboxylic acid imide ester (I) may, except for the case where $R^2$ and $R^3$ and/or $R^4$ and $R^5$, in combination, each form a methylene group which may be substituted, also be produced by the following steps.

(1) A long chain carboxylic acid (II) is subjected to dehydration condensation with an equimolar amount of benzyl alcohol in the presence of DCC, to yield a long chain dicarboxylic acid monobenzyl ester (hereinafter referred to as "long chain dicarboxylic acid monobenzyl ester (IV)") represented by the following general formula (IV)

(IV)

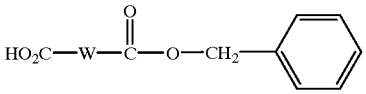

wherein W is as defined above.

(2) The long chain dicarboxylic acid monobenzyl ester (IV) is reacted with N-hydroximide (III) in the usual manner to give a long chain dicarboxylic acid monobenzyl monoimide ester (hereinafter referred to as "long chain dicarboxylic acid diester (V)") represented by the following general formula (V)

(V)

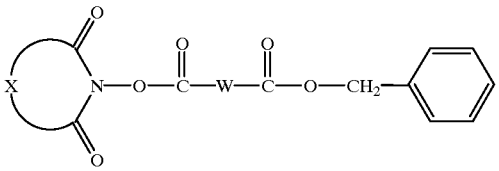

wherein W and X are as defined above.

(3) The benzyl ester part of the long chain dicarboxylic acid diester (V) is removed by hydrogenolysis in the usual manner, to obtain the desired compound.

The salt of the long chain carboxylic acid imide ester (I) is synthesized by the usual salt formation process. Where the imide part of the long chain carboxylic acid imide ester (I) forms the salt, the salt may be synthesized by conducting similar reactions to the above with a salt of N-hydroximide (III) as a starting material.

The long chain carboxylic acid imide ester (I) or its salts of the present invention (hereinafter referred to as "long chain carboxylic acid imide ester derivative") is useful as chemical modifier of proteins.

The long chain carboxylic acid imide ester derivative is reacted with a protein in an aqueous solution at a pH of 6 to 10 to yield a protein derivative represented by the following formula

[protein][Z]n wherein [protein] represents a protein having n amino residues each derivable from amino group by removal of one of its hydrogen atoms, instead of amino groups, [Z] is a residue (hereinafter referred to as "long chain carboxylic acid residue") represented by the following general formula

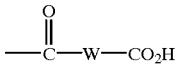

wherein W is as defined above, and derivable from a long chain dicarboxylic acid (II) by removal of a hydroxyl group from one of its carboxyl groups, and n represents an average of the number of amide bonds between [Z] and [protein], which is in a range of 1 to 8.

The reaction of the long chain carboxylic acid imide ester derivative with a protein is, although details differ more or less depending on the type of the protein, generally conducted by dissolving the protein in an aqueous solution of a salt such as sodium carbonate, sodium hydrogencarbonate, sodium acetate or sodium phosphate, and adding to the obtained solution the long chain carboxylic acid imide ester derivative in the powder form or in the form of a solution in an organic solvent such as dimethyl sulfoxide. It is necessary to maintain the pH of the solution within a range of 6 to 10 during the reaction. If the pH is lower than 6, the solubility of the long chain carboxylic acid imide ester derivative will decrease, whereby the reaction hardly proceeds. If the pH is higher than 10, the protein will be inactivated in most cases so that it becomes difficult to effectively obtain the protein derivatives of the present invention. The reaction temperature is preferably not more than the denaturation temperature of the protein and generally about 3° to 50° C., more preferably about 3° to 40° C. The reaction time is, while varying depending on the reaction temperature and the way how the long chain carboxylic acid imide ester derivative is added, generally in a range of about 10 to 30 days. The amount used of the long chain carboxylic acid imide ester derivative is about 1 to 100 moles based on 1 mole of the protein. Where SOD is used as protein, the amount of the long chain carboxylic acid imide ester derivative is preferably about 2 to 50 moles based on 1 mole of SOD. The amount used can control the number of molecules of the long chain carboxylic acid residue bounded to the protein.

The reaction mixture thus obtained contains the resulting protein derivative, unreacted protein, the long chain carboxylic acid imide ester derivative and the like. The reaction mixture is filtered and the filtrate is then subjected to gel filtration. The obtained eluate containing the protein derivative is as required subjected to hydrophobic chromatography, ion-exchange chromatography or the like and concentrated by ultrafiltration, and is subjected to lyophilization, to give the protein derivative in the solid form.

In the above reaction, the amino groups of the protein react with the long chain carboxylic acid imide ester derivative, to form the protein derivative.

The protein derivative obtained by the above reaction is a mixture of those obtained by reacting the protein with one or more molecules of the long chain carboxylic acid imide ester derivative, so that the numbers of the long chain carboxylic acid residue contained in 1 molecule of the protein derivative are not the same. In the above general formula representing a protein derivative, n therefore means an average value of the numbers of the long chain carboxylic acid residues bonded to 1 molecule of the protein. If however a protein derivative in which the numbers of the long chain carboxylic acid residues bonded to 1 molecule of the protein are the same is desired, it can be obtained by subjecting the protein derivative obtained by the above process further to gel filtration, ion-exchange chromatography or like processes. In the above reaction and processes after the reaction, the carboxyl groups present in the protein derivative may form alkali metal salts or ammonium salts. The protein derivative containing carboxyl groups in salt form can also be used as effective ingredient of medicines without any problem.

The protein derivative contain 1 to 8 long chain carboxylic acid residues bonded to 1 molecule of the protein and has a significantly prolonged plasma half-life as compared to the unmodified protein. Among protein derivatives, neocarzinostatin (hereinafter referred to as "NCS") derivative is, in view of prolongation of plasma half-life and determinability of chemical structure, desirably modified with the long chain carboxylic acid imide ester derivative at its 1-position alanine and at its 20-position lysine.

Examples of the protein used as the starting material for the above reaction are as follows.

Asparaginase, arginase, interleukin-1, IL-2, interleukin-3, interleukin-4, interleukin-5, interleukin-6, interleukin-7, interleukin-8, urokinase, prourokinase, streptokinase, TPA, β-glucosidase, β-glucuronidase, α-galactosidase, adenosine deaminase, uricase, SOD, insulin, bilirubin oxidase, G-CSF, granulocyte macrophage colony-stimulating factor, macrophage colony-stimulating factor, NCS, catalase, elastase, erythropoietin, interferon-α, interferon-β, interferon-γ, tumor necrosis factor-α, tumor necrosis factor-β, nerve growth factor, epidermal growth factor, ovalbumin, platelet derived growth factor, thrombomodulin, α1-antitrypsin, bone morphogenetic protein, cartilage derived factor, fibroblast growth factor, growth hormone, transforming growth factor-β(TGF-β), blood coagulation factor IX, protein C, protein S, insulin-like growth factor, calcitonin, somatostatin, tissue inhibitor of metalloproteinase (TIMP), atrial natriuretic hormone, CD-4 protein, cystatin, calpastatin, urinastatin and parathyroid hormone.

The long chain carboxylic acid imide ester derivative of the present invention has a fatty acid portion. The protein derivative modified by such long chain carboxylic acid imide ester therefore is capable of reversibly binding plasma protein and biological membrane, whereby it has prolonged plasma half-life and the feature of good delivery to organs.

It is preferable that, in the long chain carboxylic acid imide ester, the long chain hydrocarbon residue represented by W have 8 to 28, more preferably 10 to 20 principal chain atoms. Where SOD is modified, it is particularly preferred that the number of principal chain atoms of the long chain hydrocarbon residue represented by W be 10 to 15. If a long chain carboxylic acid imide ester with the number of principal chain atoms being less than 8 is reacted with protien, the resulting protein derivative will have poor affinity to plasma protein. If the number is larger than 28, the long chain carboxylic acid imide ester will have poor solubility in an aqueous solution with a pH of 6 to 10, whereby it becomes difficult to bond such long chain carboxylic acid imide ester to protein.

The protein derivative effectively exhibits the pharmacological effect inherent to the unmodified protein. For example, SOD derivative has, as is apparent from the results obtained in Test Examples 2 which will be described later herein, excellent anti-ulcer activity, and also has pharmacological activities such as anti-inflammatory, anti-ischemic and cerebral edema-preventing activities. NCS derivative has excellent anti-cancer activity.

Toxicological studies have shown the low toxicity of the protein derivatives.

The above results show that the protein derivatives are effective for treating or preventing various diseases corresponding to the pharmacological activities known to be inherent to the unmodified protein.

SOD derivatives are effective for diseases caused by active oxygen species, and can be used in particular as anti-inflammatory agents, anti-ulcer agents, anti-ischemic agents, cerebral edema-preventing agents, anti-paraquat intoxication agents, etc. and are also useful as drugs to alleviate various side effects induced by anti-cancer agents, as caused by active oxygen species. Further, the SOD derivatives are useful as therapeutic agents for treating dermal diseases such as burn, trauma and various dermatides. The SOD derivatives more effectively retain the pharmacological activities inherent to unmodified SOD [Saishin Igaku, 39, No. 2, 339 (1984); Igaku to Yakugaku, 14, No. 1, 55 (1985); Jikken Igaku, 4, No. 1 (1986) "Tokushuh: Seitainai Furii Rajikaru to Shikkan" (Special Number: Free Radicals and Diseases); Fragrance Journal, 79, 89 (1986)]. Moreover, the SOD derivatives have pharmacological activities against those diseases caused by active oxygen species and those against which unmodified SOD shows no pharmacological activities.

NCS derivatives are useful as anti-cancer agents.

The dosage of the protein derivative depends on the kind of disease, severity of the disease, patient's tolerance and other factors. For example, the usual daily dosage of SOD derivative for adult humans is 0.1 to 500 mg and preferably 0.5 to 100 mg. The dosage of NCS derivative varies depending on the method of administration, malignancyand type of the cancer, patient's condition of disease and general observation, severity of the cancer and the like, but is generally 0.1 to 100 mg for adult human and preferably 0.1 to 10 mg. The dosage is appropriately administered either in a single dose or in a few divided doses. Upon administration various dosage forms may be taken suitable for the respective routes of administration. The NCS derivative can be administered directly to local intra-tissue such as originally developed part of cancer or the part where an cancer has been enucleated by surgery, or administered intracutaneously, subcutaneously, intramascularly, intravenously, intraarticularly, orally or the like, or by external administration such as external application, spraying, suppository or by insertion intourinary bladder.

The protein derivative can be formulated and prepared by the established pharmaceutical procedures into pharmaceutical compositions. Such pharmaceutical compositions can be manufactured using pharmaceutically acceptable carriers, vehicles and other auxiliary substances which are commonly used in pharmaceutical practice.

When such pharmaceutical compositions are intended for oral administration, they are preferably provided in dosage forms suitable for absorption from the gastrointestinal tract. Tablets and capsules which are unit dosage forms for oral administration may contain binders such as syrup, gum arabic, gelatin, sorbitol, gum tragacanth and polyvinylpyrrolidione; excipients such as lactose, corn starch, calcium phosphate, sorbitol and glycine; lubricants such as magnesium stearate, talc, polyethylene glycol and silica; disintegrators such as potato starch; pharmaceutically acceptable wetting agents such as sodium laurylsulfate and so on. The tablets may be coated in the well-known manner. Liquid preparation for oral administration may be aqueous or oily suspensions, solutions, syrups, elixirs and so on, or may be lyophilisates which are extemporaneously reconstituted with water or other suitable vehicles before use. Such liquid preparations may contain the usual additives inclusive of suspending agents such as sorbitol syrup, methylcellulose, glucose/sucrose syrup, gelatin, hydroxyethylcellulose, carboxymethylcellulose, aluminum stearate gel and hydrogenated edible oils and fats; emulsifiers such as lecithin, sorbitan monooleate and gum arabic; non-aqueous vehicles such as almond oil, fractionated coconut oil, oleaginous esters, propylene glycol and ethanol; preservatives such as methyl p-hydroxybenzoate, propyl p-hydroxybenzoate and sorbic acid; and so forth.

For preparing injections, the protein derivative is dissolved in an suitable solvent such as physiological saline and glucose solution for injection; and the SOD derivative concentration is adjusted to 2 to 20 mg per 2 to 10 ml of solvent in a conventional manner to give injections for subcutaneous, intramuscular or intravenous administration. In preparing the above injections, pH-adjusting agents, buffers, stabilizers, preservatives, solubilizer and so forth may be added to the aqueous solution, if necessary.

The above-mentioned pharmaceutical composition can contain the protein derivative in a concentration selected according to the form thereof and other factors, generally in a concentration of about 0.01 to 50% by weight, preferably about 0.1 to 20% by weight.

Other features of the invention will become apparent in the course of the following descriptions of exemplary embodiments which are given for illustration of the invention and are not intended to be limiting thereof.

In the Examples that follow, $^1$H-NMR was measured using tetramethylsilane as internal standard. IR absorption spectrum was measured by KBr disk method.

EXAMPLES

Example 1

Synthesis of N-(13-carboxytridecanoyloxy) succinimide

In 15 ml of anhydrous tetrahydrofuran 1,14-tetradecanedioic acid (1.0 g, 3.87 mmoles) was dissolved. To the obtained solution, were added a solution of N-hydroxysuccinimide (445 mg, 3.87 mmoles) in 5 ml of anhydrous tetrahydrofuran and N,N-dimethylaminopyridine hydrochloride (3.1 mg, 0.02 mmole) and the mixture was stirred for 30 minutes. To the mixture was added a solution of DCC (799 mg, 3.87 mmoles) in 5 ml of anhydrous tetrahydrofuran and the resulting mixture was stirred overnight. The reaction mixture was filtered and the filtrate was concentrated under reduced pressure. The residue was separated and purified by silica gel chromatography [eluent: mixture of benzene and chloroform (volume ratio): 1:3], to give N-(13-carboxytridecanoyloxy)succinimide (510 mg, 37%) having the following properties.

m.p. 116°–118° C.

FD-MS (m/z): $[M+H]^+$ 356

$^1$H-NMR ($CDCl_3$, 270 MHz): δ 1.18–1.47 (m, 16H), 1.63 (m, 2H) 1.74 (m, 2H), 2.35 (t, 2H), 2.57 (t, 2H), 2.84 (s, 4H), 7.85–10.50 (br, 1H).

IR ($cm^{-1}$): 2920, 2850, 1825, 1790, 1740, 1725, 1710, 1210, 1070

Example 2

Synthesis of N-(15-carboxypentadecanoyloxy) succinimide

In 30 ml of anhydrous tetrahydrofuran 1,16-hexadecanedioic acid (1.0 g, 3.49 mmoles) was dissolved. To the obtained solution, were added a solution of N-hydroxysuccinimide (402 mg, 3.49 mmoles) in 10 ml of anhydrous tetrahydrofuran and N,N-dimethylaminopyridine hydrochloride (2.8 mg, 0.018 mmole) and the mixture was stirred for 30 minutes. To the mixture was added a solution of DCC (720 mg, 3.49 mmoles) in 10 ml of anhydrous tetrahydrofuran and the resulting mixture was stirred overnight. The reaction mixture was filtered and the filtrate was concentrated under reduced pressure. The residue was separated and purified by silica gel chromatography [eluent: mixture of benzene and chloroform (volume ratio): 1:3], to give N-(15-carboxypentadecanoyloxy)succinimide (429 mg, 32%) having the following properties.

m.p. 118.5°–121° C.

FD-MS (m/z): $[M+H]^+$ 384

$^1$H-NMR ($CDCl_3$, 270 MHz): δ 1.18–1.45 (m, 20H), 1.62 (m, 2H) 1.74 (m, 2H), 2.34 (t, 2H), 2.60 (t, 2H), 2.84 (s, 4H).

IR ($cm^{-1}$): 2920, 2850, 1825, 1790, 1740, 1725, 1710, 1210, 1070

Example 3

Synthesis of N-(17-carboxyheptadecanoyloxy) succinimide

In 30 ml of anhydrous tetrahydrofuran 1,18-octadecanedioic acid (1.0 g, 3.18 mmoles) was dissolved. To the obtained solution, were added a solution of N-hydroxysuccinimide (366 mg, 3.18 mmoles) in 10 ml of anhydrous tetrahydrofuran and N,N-dimethylaminopyridine hydrochloride (2.5 mg, 0.016 mmole) and the mixture was stirred for 30 minutes. To the mixture was added a solution of DCC (656 mg, 3.18 mmoles) in 10 ml of anhydrous tetrahydrofuran and the resulting mixture was stirred overnight. The reaction mixture was filtered and the filtrate was concentrated under reduced pressure. The residue was separated and purified by silica gel chromatography [eluent: mixture of benzene and chloroform (volume ratio): 1:3.5], to give N-(17-carboxyheptadecanoyloxy)succinimide (480 mg, 37%) having the following properties.

m.p. 120°–122.5° C.

FD-MS (m/z): $[M+H]^+$ 412

$^1$H-NMR ($CDCl_3$, 270 MHz): δ 1.13–1.47 (m, 24H), 1.63 (m, 2H) 1.75 (m, 2H), 2.34 (t, 2H), 2.60 (t, 2H), 2.84 (s, 4H), 5.0–7.0 (br, 1H).

IR ($cm^{-1}$): 2920, 2850, 1825, 1790, 1740, 1725, 1710, 1210, 1070

Example 4

Synthesis of N-(9-carboxynonadecanoyloxy) succinimide

In 50 ml of anhydrous tetrahydrofuran 1,20-eicosanedioic acid (1.0 g, 2.92 mmoles) was dissolved. To the obtained solution, were added a solution of N-hydroxysuccinimide (336 mg, 2.92 mmoles) in 10 ml of anhydrous tetrahydrofuran and N,N-dimethylaminopyridine hydrochloride (2.3 mg, 0.015 mmole) and the mixture was stirred for 30 minutes. To the mixture was added a solution of DCC (602 mg, 2.92 mmoles) in 10 ml of anhydrous tetrahydrofuran and the resulting mixture was stirred overnight. The reaction mixture was filtered and the filtrate was concentrated under reduced pressure. The residue was separated and purified by silica gel chromatography [eluent: mixture of benzene and chloroform (volume ratio): 1:3.5], to give N-(19-carboxynonadecanoyloxy)succinimide (420 mg, 33%) having the following properties.

m.p. 121.5°–124° C.

FD-MS (m/z): $[M+H]^+$ 440

$^1$N-NMR ($CDCl_3$, 270 MHz): δ 1.14–1.45 (m, 28H), 1.63 (m, 2H), 1.74 (m, 2H), 2.35 (t, 2H), 2.60 (t, 2H), 2.84 (s, 4H).

IR ($cm^{-1}$): 2920, 2850, 1825, 1790, 1740, 1725, 1710, 1210, 1070

Example 5

Synthesis of N-(21-carboxyheneicosanoyloxy) succinimide

In 70 ml of anhydrous tetrahydrofuran 1,22-docosanedioic acid (1.0 g, 2.70 mmoles) was dissolved. To the obtained solution, were added a solution of N-hydroxysuccinimide (311 mg, 2.70 mmoles) in 10 ml of anhydrous tetrahydorfuran and N,N-dimethylaminopyridine hydrochloride (2.1 mg, 0.014 mmole) and the mixture was stirred for 30 minutes. To the mixture was added a solution of DCC (602 mg, 2.70 mmoles) in 10 ml of anhydrous tetrahydrofuran and the resulting mixture was stirred overnight. The reaction mixture was filtered and the filtrate was concentrated under reduced pressure. The residue was separated and purified by silica gel chromatography [eluent: mixture of benzene and chloroform (volume ratio): 1:3.5], to give N-(21-carboxyheneicosanoyloxy)succinimide (440 mg, 35%) having the following properties.

m.p. 122°–124.5° C.

FD-MS (m/z): $[M+H]^+$ 468

$^1$H-NMR ($CDCl_3$, 270 MHz): δ 1.12–1.43 (m, 16H), 1.63 (m, 2H), 1.74 (m, 2H), 2.34 (t, 2H), 2.60 (t, 2H), 2.84 (s, 4H).

IR ($cm^{-1}$): 2920, 2850, 1825, 1790, 1740, 1725, 1710, 1210, 1070

Example 6

(a) Synthesis of 1,14-tetradecanedioic acid monobenzyl ester

In 80 ml of anhydrous tetrahydrofuran 1,14-tetradecanedioic acid (5.0 g, 19.4 mmoles) was dissolved. To the obtained solution, were added a solution of benzyl alcohol (2.1 g, 19.4 mmoles) in 10 ml of tetrahydrofuran and N,N-dimethylaminopyridine hydrochloride (15 mg, 0.1 mmole) and mixture was stirred fo 30 minutes. To the mixture was added a solution of DCC (4.0 g, 19.4 mmoles) in 10 ml of anhydrous tetrahydrofuran and the resulting mixture was stirred at a room temperature for 20 hours. The reaction mixture was filtered and the filtrate was concentrated under reduced pressure. The residue was separated and purified by silica gel chromatography [eluent: mixture of hexane and diethyl ether (volume ratio): 2:1], to give 1,14-tetradecanedioic acid monobenzyl ester (2.42 g, 38%) having the following properties.

m.p. 73.5°–74° C.

$^1$H-NMR ($CDCl_3$, 270 MHz): δ 1.17–1.40 (m, 16H), 1.50–1.70 (m, 4H), 2.23–2.39 (m, 4H), 5.11 (s, 2H), 7.32 (m, 5H), 7.40–9.35 (br, 1H).

(b) Synthesis of N-(13-benzyloxycarbonyltridecanoyloxy)succinimide

In 30 ml of tetrahydrofuran 1,14-tetradecanedioic acid monobenzyl ester (2.4 g, 6.89 mmoles) was dissolved. To the obtained solution, were added a solution of N-hydroxysuccinimide (793 mg, 6.89 mmoles) in 15 ml of anhydrous tetrahydrofuran and N,N-dimethylaminopyridine hydrochloride (3.3 mg, 0.02 mmole) and the mixture was stirred for 30 minutes at a room temperature. To the mixture was added a solution of DCC (1.42 g, 6.89 mmoles) in 15 ml of tetrahydrofuran and the resulting mixture was stirred at a room temperature for 15 hours. The reaction mixture was filtered and the filtrate was concentrated under reduced pressure. The residue was separated and purified by silica gel chromatography [eluent: mixture of hexane and ethyl acetate (volume ratio): 2:1], to give N-(13-benzyloxycarbonyltridecanoyloxy)succinimide (2.31 mg, 75%) having the following properties.

m.p. 61.5°–62.5° C.

$^1$H-NMR ($CDCl_3$, 270 MHz): δ 1.05–1.46 (m, 16H), 1.63 (m, 2H) 1.72 (m, 2H), 2.33 (t, 2H), 2.58 (t, 2H), 2.79 (s, 4H), 5.11 (s, 2H), 7.33 (m, 5H).

(c) Synthesis of N-(13-carboxytridecanoyloxy) succinimide

In 15 ml of tetrahydrofuran N-(13-benzyloxycarbonyltridecanoyloxy)succinimide (2.28 g, 5.12 mmoles) was dissolved. To the obtained solution, were added 228 mg of 10% palladium carbon and the mixture was stirred for 15 hours under an atmosphere of hydrogen. The reaction mixture was filtered and the filtrate was concentrated under reduced pressure. The residue was recrystallized from ethanol, to give N-(13-carboxytridecanoyloxy) succinimide (1.71 mg, 94%) having the following properties.

m.p. 116°–118° C.

FD-MS (m/z): $[M+H]^+$ 356

$^1$H-NMR ($CDCl_3$, 270 MHz): δ 1.18–1.47 (m, 16H), 1.63 (m, 2H), 1.74 (m, 2H), 2.35 (t, 2H), 2.57 (t, 2H), 2.84 (s, 4H), 7.85–10.50 (br, 1H).

IR ($cm^{-1}$): 2920, 2850, 1825, 1790, 1740, 1725, 1710, 1210, 1070

Example 7

Synthesis of N-(15-carboxypentadecanoyloxy) phthalimide

In 15 ml of anhydrous tetrahydrofuran 1,16-hexadecanedioic acid (500 mg, 1.75 mmoles) was dissolved. To the obtained solution, were added a solution of N-hydroxyphthalimide (285 mg, 1.75 mmoles) in 10 ml of anhydrous tetrahydrofuran and N,N-dimethylaminopyridine hydrochloride (1.4 mg) and the mixture was stirred for 30 minutes. To the mixture was added a solution of DCC (361 mg, 1.75 mmoles) in 3 ml of anhydrous tetrahydrofuran and the resulting mixture was stirred overnight. The reaction mixture was filtered and the filtrate was concentrated under reduced pressure. The residue was separated and purified by silica gel chromatography, to give N-(15-carboxypentadecanoyloxy)phthalimide (310 mg, 41%) having the following properties.

m.p. 109°–110.5° C.

FD-MS (m/z): $[M+H]^+$ 432

$^1$H-NMR ($CDCl_3$, 270 MHz): δ 1.14–1.50 (m, 20H), 1.63 (m, 2H), 1.78 (m, 2H), 2.34 (t, 2H), 2.66 (t, 2H), 7.72–7.94 (m, 4H).

Example 8

Synthesis of N-(15-carboxypentadecanoyloxy) tetramethylphthalimide

In 3 ml of anhydrous tetrahydrofuran 1,16-hexadecanedioic acid (100 mg, 0.35 mmoles) was dissolved.

To the obtained solution, were added a solution of N-hydroxytetramethylphthalimide (77 mg, 0.35 mmoles) in 2 ml of anhydrous tetrahydrofuran and N,N-dimethylaminopyridine hydrochloride (0.3 mg) and the mixture was stirred for 30 minutes. To the mixture was added a solution of DCC (72 mg, 0.35 mmoles) in 0.5 ml of anhydrous tetrahydrofuran and the resulting mixture was stirred overnight. The reaction mixture was filtered and the filtrate was concentrated under reduced pressure. The residue was separated and purified by silica gel chromatography, to give N-(15-carboxypentadecanoyloxy)-tetramethylphthalimide (58 mg, 34%) having the following properties.

FD-MS (m/z): $[M+H]^+$ 488

$^1$H-NMR ($CDCl_3$, 270 MHz): δ 1.14–1.49 (m, 20H), 1.61 (m, 2H) 1.78 (m, 2H), 2.29 (s, 6H), 2.34 (t, 2H), 2.66 (t, s, 8H).

Example 9

Synthesis of N-(15-carboxypentadecanoyloxy)-5-norbornene-2,3-dicarboximide

Example 7 was repeated except for using, instead of N-hydroxyphthalimide (285 mg, 1.75 mmoles), N-hydroxy-5-norbornene-2,3-dicarboximide (313 mg, 11.75 mmoles) to obtain N-(15-carboxypentadecanoyloxy)-5-norbornene-2,3-dicarboximide (340 mg, 44%) having the following properties.

m.p. 103°–104.5° C.

FD-MS (m/z): $[M+H]^+$ 448

$^1$H-NMR ($CDCl_3$, 270 MHz): δ 1.14–1.43 (m, 20H), 1.48–1.82 (m, 6H), 2.34 (t, 2H), 2.52 (t, 2H) 3.32 (s, 2H), 3.44 (s, 2H) 6.19 (s, 2H).

Example 10

(a) Synthesis of N-(15-benzyloxycarbonylpentadecanoyloxy)-tartrimide

In 1.5 ml of tetrahydrofuran N-hydroxytartrimide (59 mg, 0.40 mmole) was dissolved. To the obtained solution, were added a solution of 1,16-hexadecanedioic acid monobenzyl ester (150 mg, 0.40 mmole) and a solution of DCC (83 mg, 0.40 mmole) in 0.5 ml of tetrahydrofuran and the resulting mixture was stirred overnight at 4° C. The reaction mixture was filtered and the filtrate was concentrated under reduced pressure. The residue was separated and purified by silica gel chromatography, to give N-(15-benzyloxycarbonylpentadecanoyloxy)tartrimide (7 mg, 4%) having the following properties.

$^1$H-NMR ($CDCl_3$, 270 MHz): δ 1.14–1.45 (m, 20H), 1.51–1.80 (m, 4H), 2.34 (t, 2H), 2.59 (t, 2H), 3.28 (br, 2H), 4.73 (s, 2H), 5.11 (s, 2H), 7.33 (s, 5H).

(b) Synthesis of N-(15-carboxypentadecanoyloxy) tartrimide

In 1 ml of tetrahydrofuran N-(15-benzyloxycarbonylpentadecanoyloxy)tartrimide (7 mg, 0.0014 mmole) was dissolved. To the obtained solution, was added 1 mg of 10% palladium carbon and the mixture was stirred for 1 hour under an atmosphere of hydrogen. The reaction mixture was filtered and the filtrate was concentrated under reduced pressure, to give N-(15-carboxypentadecanoyloxy)tartrimide (5 mg, 87%) having the following properties.

FD-MS (m/z): $[M+H]^+$ 416

$^1$H-NMR (DMSO-$d_6$, 270 MHz): δ 1.05–1.40 (m, 20H), 1.48 (m, 2H), 1.62 (m, 2H), 2.18 (t, 2H), 2.51 (t, 2H), 4.51 (br, 2H), 6.10–7.50 (br, 1H).

Example 11

(a) Synthesis of N-(13-benzyloxycarbonyltridecanoyloxy)sulfosuccinimide sodium salt In 0.4 ml of anhydrous dimethyl formamide was dissolved 1,14-tetradecanedioic acid monobenzyl ester (100 mg, 0.29 mmole). To the obtained solution were added sodium N-hydroxysulfosuccinimide (63 mg, 0.29 mmole) and a solution of DCC (65 mg, 0.29 mmole) in 0.4 ml of anhydrous dimethylformamide and the resulting mixture was stirred for 14 hours at a room temperature. The reaction mixture was filtered and the filtrate was stirred for 2 hours at a temperature under ice cooling. The solid that formed was collected by filtration and dried under reduced pressure to give N-(13-benzyloxycarbonyltridecanoyloxy) sulfosuccinimide sodium salt (66 mg, 42%) having the following properties.

$^1$H-NMR (DMSO-$d_6$, 270 MHz): δ 1.13–1.42 (m, 16H), 1.47–1.68 (m, 4H), 2.33 (t, 2H), 2.63 (t, 2H), 2.87 (d, 1H) 3.14 (m, 1H), 3.94 (m, 1H) 5.08 (s, 2H), 7.34 (s, 5H).

(b) Synthesis of N-(13-carboxytridecanoyloxy) sulfosuccinimide sodium salt

In 1 ml of dimethylformamide was dissolved N-(13-benzyloxycarbonyltridecanoyloxy)sulfosuccinimide sodium salt (50 mg, 0.11 mmole). To the obtained solution, was added 5 mg of 10% palladium carbon and the mixture was stirred for 20 hours under an atmosphere of hydrogen. The reaction mixture was filtered and to the filtrate 30 ml of ethyl acetate was added. The mixture was stirred for 30 minutes and the solid that formed was collected by filtration and dried under reduced pressure to give N-(13-carboxytridecanoyloxy)sulfosuccinimide sodium salt (22 mg, 63%) having the following properties.

FAB-MS (m/z): 480, 458, 435, 413

$^1$H-NMR (DMSO-$d_6$, 270 MHz): δ 1.15–1.39 (m, 16H), 1.47 (m, 2H), 1.60 (m, 2H), 2.17 (t, 2H), 2.63 (t, 2H), 2.87 (d, 1H), 3.14 (m, 1H), 3.94 (m, 1H).

Example 12

Synthesis of N-(15-carboxypentadecanoyloxy)-3-isopropylsuccinimide

Example 8 was repeated except for using, instead of N-hydroxytetramethylphthalimide (77 mg, 0.35 mmoles), N-hydroxy-3-isopropylsuccinimide (55 mg, 0.35 mmoles) to obtain N-(15-carboxypentadecanoyloxy)-3-isopropylsuccinimide (42 mg, 28%) having the following properties.

FD-MS (m/z): $[M+H]^+$ 426

$^1$H-NMR ($CDCl_3$, 270 MHz): δ 0.80 (d, 3H), 1.00 (d, 3H) 1.18–1.45 (m, 20H), 1.62 (m, 2H), 1.74 (m, 2H) 2.34 (m, 3H), 2.55 (dd, 1H) 2.60 (t, 2H), 2.79 (dd, 1H) 2.91 (m, 1H).

Example 13

Synthesis of N-(15-carboxypentadecanoyloxy) tetramethylsuccinimide

Example 8 was repeated except for using, instead of N-hydroxytetramethylphthalimide (77 mg, 0.35 mmoles), N-hydroxytetramethylsuccinimide (60 mg, 0.35 mmoles) to obtain N-(15-carboxypentadecanoyloxy) tetramethylsuccinimide (40 mg, 26%) having the following properties.

FD-MS (m/z): $[M+H]^+$ 440

$^1$H-NMR ($CDCl_3$, 270 MHz): δ 1.18–1.46 (m, 32H), 1.62 (m, 2H), 1.74 (m, 2H) 2.34 (t, 2H), 2.60 (t, 2H)

Example 14

Synthesis of N-(15-carboxypentadecanoyloxy)-3-benzylsuccinimide

Example 8 was repeated except for using, instead of N-hydroxytetramethylphthalimide (77 mg, 0.35 mmoles), N-hydroxy-3-benzylsuccinimide (72 mg, 0.35 mmoles) to obtain N-(15-carboxypentadecanoyloxy)-3-benzylsuccinimide (45 mg, 27%) having the following properties.

FD-MS (m/z): $[M+H]^+$ 474

$^1$H-NMR ($CDCl_3$, 270 MHz): δ 1.18–1.45 (m, 20H), 1.62 (m, 2H), 1.74 (m, 2H) 2.30–2.92 (m, 9H), 7.06 (s, 5H).

Example 15

Synthesis of N-(15-carboxypentadecanoyloxy) itaconimide

Example 8 was repeated except for using, instead of N-hydroxytetramethylphthalimide (77 mg, 0.35 mmoles), N-hydroxyitaconimide (44 mg, 0.35 mmoles) to obtain N-(15-carboxypentadecanoyloxy)itaconimide (49 mg, 31%) having the following properties.

FD-MS (m/z): $[M+H]^+$ 396

$^1$H-NMR ($CDCl_3$, 270 MHz): δ 1.19–1.44 (m, 20H), 1.62 (m, 2H), 1.74 (m, 2H) 2.34 (t, 2H), 2.60 (t, 2H) 3.70 (t, 2H) 6.00–6.59 (m, 2H).

Example 16

Synthesis of N-(15-carboxypentadecanoyloxy) glutarimide

Example 8 was repeated except for using, instead of N-hydroxytetramethylphthalimide (77 mg, 0.35 mmoles), N-hydroxyglutarimide (45 mg, 0.35 mmoles) to obtain N-(15-carboxypentadecanoyloxy)glutarimide (40 mg, 29%) having the following properties.

FD-MS (m/z): $[M+H]^+$ 398

$^1$H-NMR ($CDCl_3$, 270 MHz): δ 1.18–1.47 (m, 20H), 1.63 (m, 2H), 1.74 (m, 2H) 2.02 (m, 2H), 2.35 (t, 2H) 2.50–2.70 (m 4H), 7.85–10.50 (br, 1H).

Reference Example 1

Synthesis of an SOD derivative by the reaction of N-(13-carboxytridecanoyloxy)succinimide with SOD To 1.4 ml of an aqueous solution human erythrocyte-type SOD (71.2 mg/ml) was added 2.6 ml of 0.5M aqueous sodium hydrogencarbonate solution (pH 8.0). To the mixture was gradually added with stirring a solution of 10.1 mg of the N-(13-carboxytridecanoyloxy)succinimide obtained in Example 6 in 0.2 ml of dimethyl sulfoxide, and the resulting mixture was stirred overnight at a room temperature. The reaction mixture was filtered and the filtrate was subjected to gel filtration using a column packed with Sephadex G-25 (trademark; Pharmacia Fine Chemicals) (eluent: 10 mM aqueous ammonium hydrogencarbonate solution) and the high-molecular-weight fractions were collected. The obtained fractions as such were subjected to ion-exchange chromatography using DEAE-Sepharose Fast Flow (trademark; Pharmacia Fine Chemicals) where elution was successively conducted with an eluent of a mixture of 10 mM Tris-hydrochloric acid butter (pH 8) and 0.15M aqueous sodium chloride solution, that of a mixture of 10 mM Tris-hydrochloric acid butter (pH 8) and 0.20M aqueous sodium chloride solution, and finally that of a mixture of 10 mM Tris-hydrochloric acid butter (pH 8) and 0.25M aqueous sodium chloride solution, to collect the corresponding fractions (hereinafter these fractions are referred to as fraction-A, fraction-B and fraction-C, respectively). These fractions were each subjected to gel filtration by using a column packed with Sephadex G-25 (eluent: 10 mM aqueous ammonium hydrogencarbonate solution), desalinized and the high-molecular-weight fractions were combined and lyophilized to give 33 mg of an SOD derivative (hereinafter referred to as SOD derivative-A), 18 mg of an SOD derivative (hereinafter referred to as SOD derivative-B), and 15 mg of an SOD derivative (hereinafter referred to as SOD derivative-C, from fraction-A, fraction-B and fraction-C, respectively. Quantitative determination of the amino groups of each of the SOD derivatives-A, -B and -C, revealed that 3.6 groups, 4.4 groups and 5.4 groups of the total amino groups in the starting material SOD had been modified, in the SOD derivatives-A, -B and -C, respectively.

Figure 2:
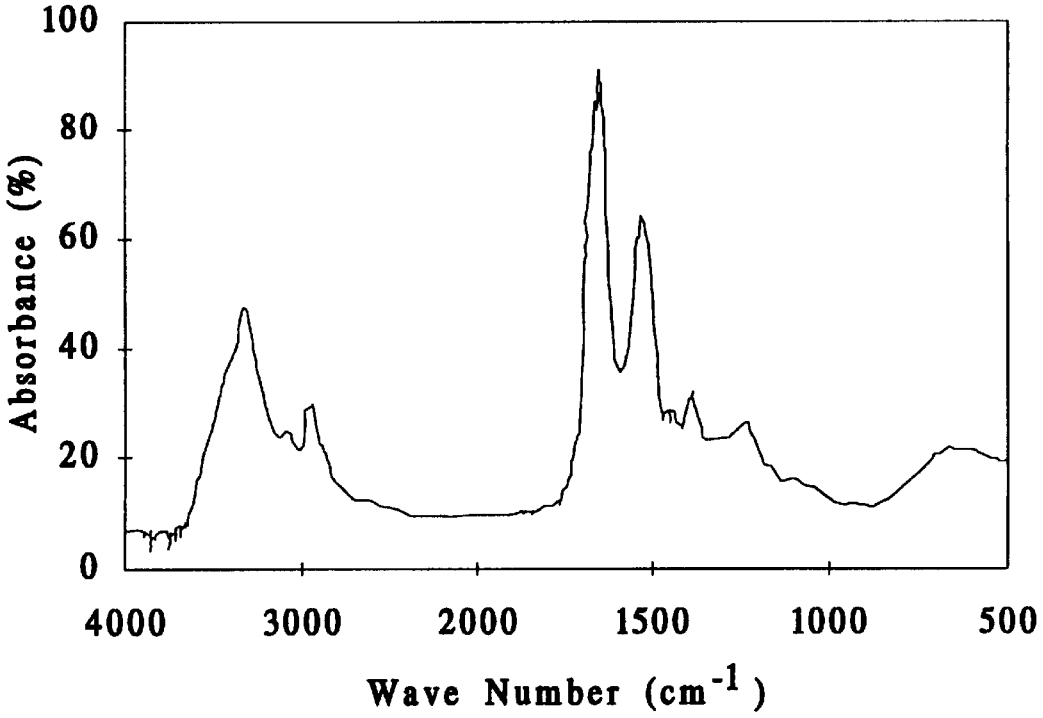
FIG. 2 shows an IR-spectrum of the SOD derivative-C obtained in Reference Example 1.

The schematic electrophorograms of the SOD used and the SOD derivative-C obtained are shown in FIG. 1(a) and (b). FIG. 2 shows an IR spectrum of the SOD derivative-C.

Reference Example 2

Synthesis of an SOD derivative by the reaction of N-(17-carboxyneptadecanoyloxy)succinimide with SOD To 1.12 ml of an aqueous solution of human erythrocyte-type SOD (71.2 mg/ml) were added 1.88 ml of water and 0.8 ml of 0.5M aqueous sodium hydrogencarbonate solution (pH 8.0). To the mixture was gradually added with stirring a solution of 3.9 mg of the N-(17-carboxyheptadecanoyloxy)succinimide obtained in Example 3 in 0.2 ml of dimethyl sulfoxide, and the resulting mixture was stirred overnight at a room temperature. The reaction mixture was filtered and the filtrate was subjected to gel filtration using a column packed with Sephadex G-25 (trademark; Pharmacia Fine Chemicals) (eluent: 10 mM aqueous ammonium hydrogencarbonate solution) and the high-molecular-weight fractions were collected. The obtained fractions as such were subjected to ion-exchange chromatography using DEAE-Sepharose Fast Flow (trademark; Pharmacia Fine Chemicals) [eluent: a mixture of 10 mM Tris-hydrochloric acid butter (pH 8) and 0.20M aqueous sodium chloride solution] and the fractions containing the resulting SOD derivative were collected. The obtained fractions were subjected to gel filtration by using a column packed with Sephadex G-25 (eluent: 10 mM aqueous ammonium hydrocarbonate solution), desalinized and the high-molecular-weight fractions were combined and lyophilized to give 18 mg of the SOD derivative. Quantitative determination by TNBS method of the amino groups in the obtained SOD derivative revealed that 2.0 pieces of the total amino groups contained in the starting material SOD had been modified.

Figure 3:
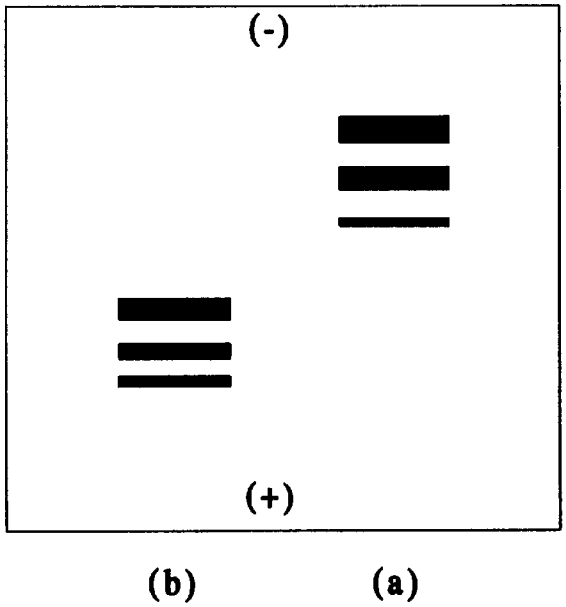
FIG. 3 shows schematic electrophorograms of (a) the SOD used in Reference Example 2 and (b) the SOD derivative obtained in Reference Example 2.
Figure 4:
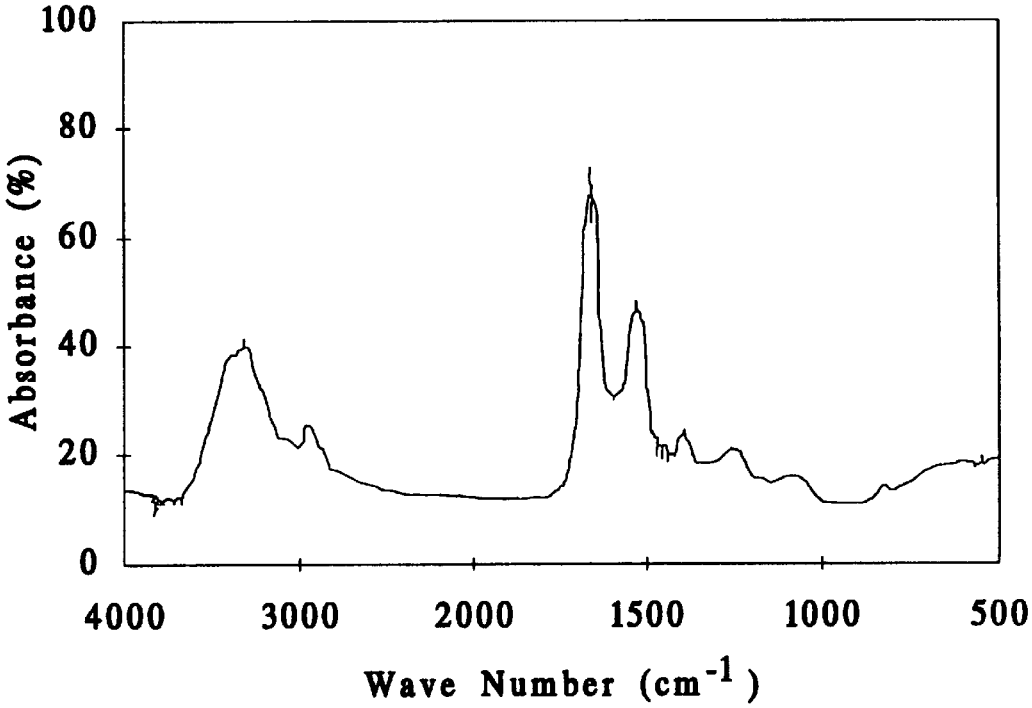
FIG. 4 shows an IR-spectrum of the SOD derivative obtained in Reference Example 2.

The schematic electrophorograms of the SOD used and the SOD derivative obtained are shown in FIG. 3(a) and (b). FIG. 4 shows an IR spectrum of the SOD derivative.

Reference Example 3

Synthesis of an SOD Derivative by the Reaction of N-(19-carboxynonadecanoyloxy)succinimide with SOD Reference Example 2 was repeated except for using, instead of 3.9 mg of N-(17-carboxyheptadecanoyoxy) succinimide, 4.1 mg of the N-(19-carboxynonadecanoyloxy) succinimide obtained in Example 4, to obtain 14 mg of an SOD derivative. Quantitative determination by TNBS method of the amino groups in the obtained SOD derivative revealed that 2.0 pieces of the total amino groups contained in the starting material SOD had been modified.

Figure 5:
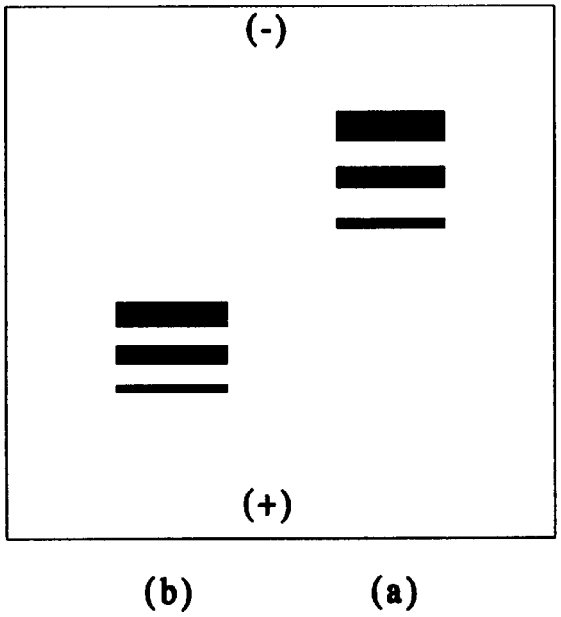
FIG. 5 shows schematic electrophorograms of (a) the SOD used in Reference Example 3 and (b) the SOD derivative obtained in Reference Example 3.
Figure 6:
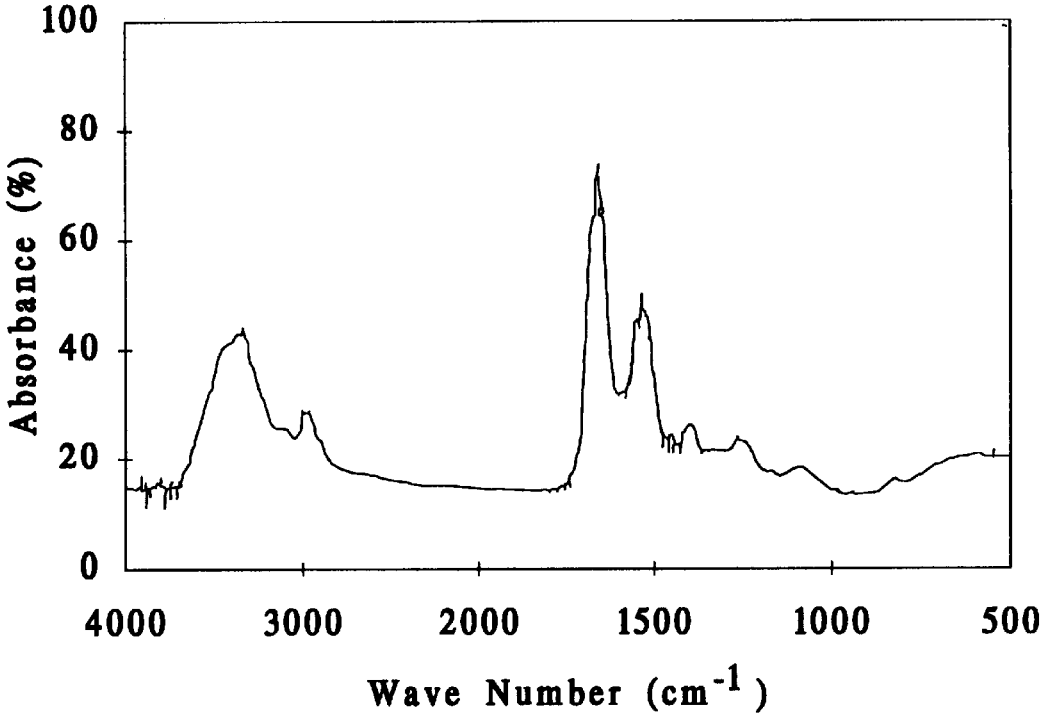
FIG. 6 shows an IR-spectrum of the SOD derivative obtained in Reference Example 3.

The schematic electrophorograms of the SOD used and the SOD derivative obtained are shown in FIG. 5(a) and (b). FIG. 6 shows an IR spectrum of the SOD derivative.

Reference Example 4

Synthesis of an NCS Derivative by the Reaction of NCS with N-(15-carboxypentadecanoyloxy) succinimide In 18 ml of a 0.5M aqueous sodium hydrogencarbonate solution was dissolved 50 mg of NCS. To the solution obtained, a solution prepared by dissolving 79.8 mg of the N-(15-carboxypentadecanoyloxy)succinimide obtained in Example 2 in 2 ml of dimethyl sulfoxide was gradually added with stirring. The mixture was stirred at 4° C. in a light-shielded placed for 2 weeks. The reaction mixture was filtered, and the filtrate was subjected to gel filtration using a column packed with Sephadex G-25 (eluent: 10 mM aqueous ammonium hydrogencarbonate solution) and the high-molecular-weight fractions were collected. The obtained fractions as such were subjected to ion-exchange chromatography using DEAE-Sepharose Fast Flow (eluent: a mixture of 10 mM Tris-hydrochloric acid butter (pH 8) and 0.20M aqueous sodium chloride solution), and the fractions containing the resulting NCS derivative were collected. The obtained fractions were subjected to gel filtration by using a column packed with Sephadex G-25 (eluent: 10 mM aqueous ammonium hydrogencarbonate solution), desalinized and the high-molecular-weight fractions were combined and lyophilized to give 7 mg of the NCS derivative. From the obtained NCS derivative no free amino group was detected by quantitative determination by TNBS method.

Figure 7:
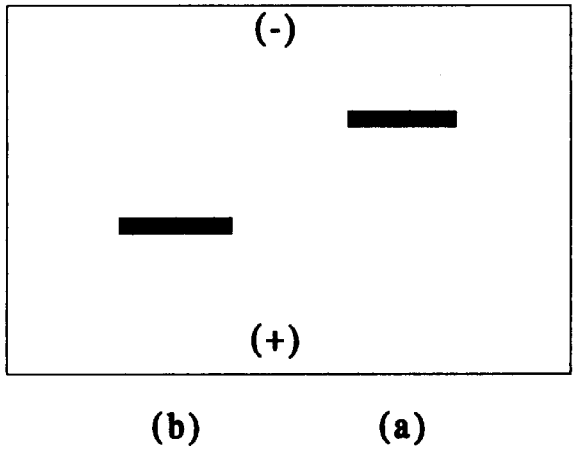
FIG. 7 shows schematic electrophorograms of (a) the NCS used in Reference Example 4 and (b) the NCS derivative obtained in Reference Example 4.
Figure 8:
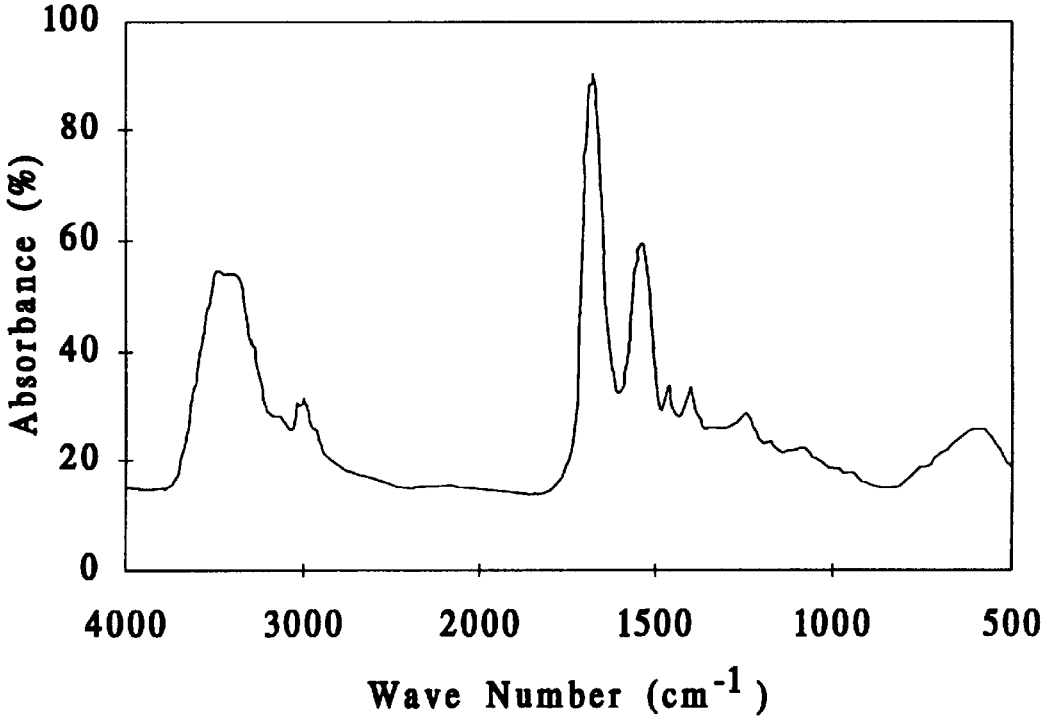
FIG. 8 shows an IR-spectrum of the NCS derivative obtained in Reference Example 4.

The schematic electrophorograms of the NCS used and the NCS derivative obtained are shown in FIG. 7(a) and (b). FIG. 8 shows an IR spectrum of the NCS derivative.

Reference Example 5

Synthesis of an NCS Derivative by the Reaction of N-(17-carboxyheptadecanoyloxy)succinimide with NCS Reference Example 4 was repeated except for using, instead of 79.8 mg of N-(15-carboxypentadecanoyloxy) succinimide, 85.6 mg of the N-(17-carboxyheptadecanoyloxy)succinimide obtained in Example 3, to obtain 5 mg of an NCS derivative. Quantitative determination by TNBS method of the amino groups in the obtained NCS derivative revealed that it contained no free amino groups.

Figure 9:
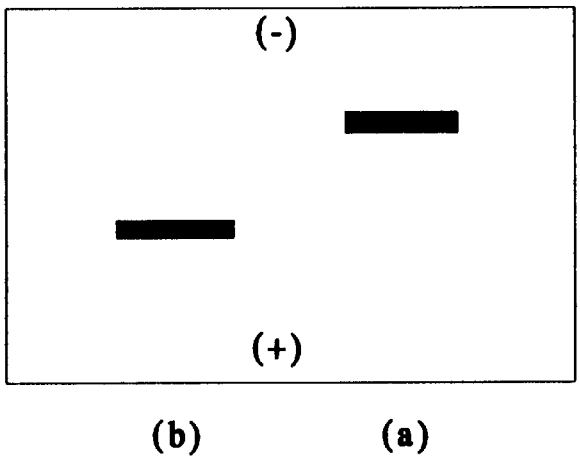
FIG. 9 shows schematic electrophorograms of (a) the NCS used in Reference Example 5 and (b) the NCS derivative obtained in Reference Example 5.
Figure 10:
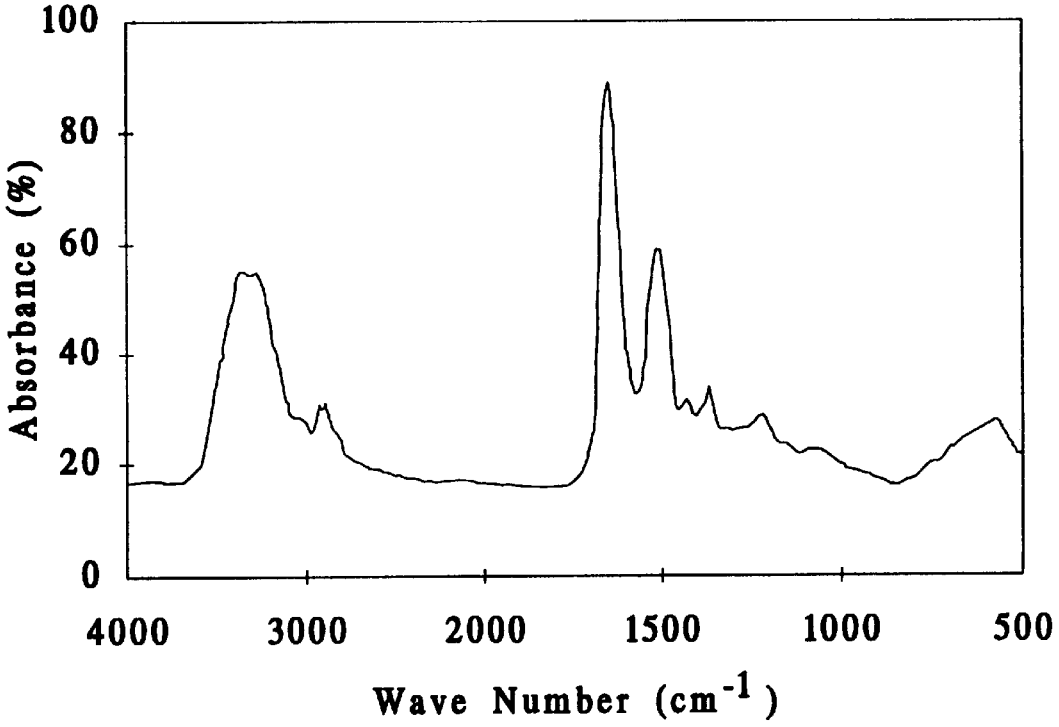
FIG. 10 shows an IR-spectrum of the NCS derivative obtained in Reference Example 5.

The schematic electrophorograms of the NCS used and the NCS derivative obtained are shown in FIG. 9 (a) and (b). FIG. 10 shows an IR spectrum of the NCS derivative.

Test Example 1

Plasma Clearance of SOD Derivatives

Figure 11:
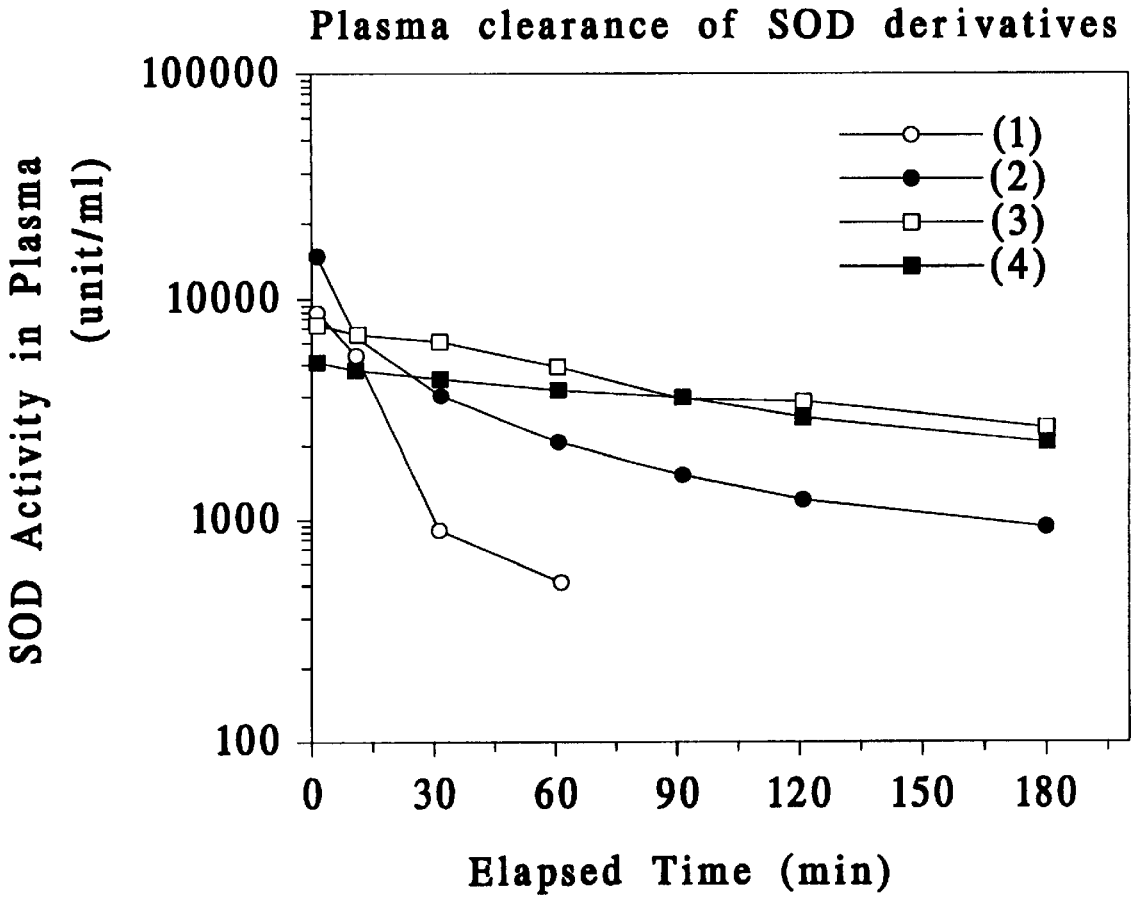
FIG. 11 shows the time courses of the plasma concentrations in Test Example 1, wherein (1), (2), (3) and (4) are for unmodified SOD, the SOD derivatives-A, -B and -C obtained in Reference Example 1, respectively.

Under pentobarbital anesthsia, rats (Wistar strain, male, 7 weeks of age, body weight about 200 g) were cannulated into the femoral vein and were heparinized intravenously (1000 U/ml, 0.2 ml/rat). Then, a specimen solution of SOD or SOD derivative in saline (10 mg/ml) was injected into the femoral vein of each rat in an amount of 0.2 ml/rat. At timed intervals, 0.2 ml blood samples were collected from the femoral vein and the time courses of plasma SOD concentrations were determined by measuring the SOD activities in plasma. The time courses of the plasma concentrations of the SOD and the SOD derivatives are shown in FIG. 11.

Test Example 2

Effect of SOD derivative on acute gastric mucosal lesion (gastric ulcer)

Male SD rats (body weight: about 200 g) were fasted overnight and were placed in restraint cages in groups of each 3 rats. The cages were vertically immersed upto the level of xyphoid process in water at 22° C. After 6 hours of stress loading, the cages were taken out from the water and the rats were exsanguinated. Their stomachs were fixed by 1% formalin. After this fixation, the lengths of linear ulcers were totaled and the sum was expressed as the ulcer index.

Rats in the control group received 0.5 ml each of saline, while rats in the test group received 0.2 ml each of a solution of the SOD derivative obtained in Reference Example 1 and weighing 2 mg/rat, all by intravenous route 5 minutes before restraint water-immersion.

The obtained results are shown in Table 1.

TABLE 1

| | Ulcer index |
|---|---|
| Control | 31.3 ± 8.1 (30.1, 23.9, 39.9) |
| Test | 14.8 ± 6.7 (16.3, 7.5, 20.6) |

As is apparent from Table 1, the SOD derivative exhibited an excellent anti-ulcer activity in the test group.

Obviously, numerous modifications and variations of the present invention are possible in light of the bore teachings. It is therefore to be understood that within the scope of the appended claims, the invention may be practiced otherwise than as specifically described herein.

What is claimed is:

1. A compound of the formula

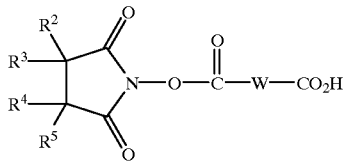

or a salt thereof, wherein W is a divalent long chain hydrocarbon radical having from 8 to 28 principal chain atoms; and wherein $R^2$, $R^3$, $R^4$ and $R^5$, in combination with the carbon atoms to which they bond, form a benzene, cyclohexane, cyclopentane, bicyclo[2.2.1]heptane, bicyclo[2.2.1]hepta-2-ene, 7-oxabicyclo[2.2.1]heptane or 7-oxabicyclo[2.2.1]hepta-2-ene ring system which is optionally substituted by —$SO_3H$, —$CO_2H$, —OH, F, Cl, Br, I, —$CH_3$ or —$OCH_3$.

2. The compound according to claim 1, wherein the divalent hydrocarbon radical W has from 10 to 20 principal chain atoms.

3. The compound according to claim 2, wherein W is a divalent radical of the formula $(CH_2)_{10}$, $(CH_2)_{11}$, $(CH_2)_{12}$, $(CH_2)_{13}$, $(CH_2)_{14}$, $(CH_2)_{15}$, $(CH_2)_{16}$, $(CH_2)_{17}$, $(CH_2)_{18}$, $(CH_2)_{19}$, $(CH_2)_{20}$, $CH_2CH{=}CH(CH_2)_7$, $(CH_2)_2CH{=}CH(CH_2)_7$, $(CH_2)_3CH{=}CH(CH_2)_7$, $(CH_2)_4CH{=}CH(CH_2)_7$, $(CH_2)_5CH{=}CH(CH_2)_7$, $(CH_2)_6CH{=}CH(CH_2)_7$, $(CH_2)_7CH{=}CH(CH_2)_7$, $(CH_2)_8CH{=}CH(CH_2)_7$, $(CH_2)_9CH{=}CH(CH_2)_7$, $(CH_2)_{10}CH{=}CH(CH_2)_7$, $(CH_2)_{11}CH{=}CH(CH_2)_7$, $(CH_2)_8CH{=}CHCH_2$, $(CH_2)_8CH{=}CH(CH_2)_2$, $(CH_2)_8CH{=}CH(CH_2)_3$, $(CH_2)_8CH{=}CH(CH_2)_4$, $(CH_2)_8CH{=}CH(CH_2)_5$, $(CH_2)_8CH{=}CH(CH_2)_6$, $(CH_2)_8CH{=}CH(CH_2)_8$, $(CH_2)_8CH{=}CH(CH_2)_9$, $(CH_2)_8CH{=}CH(CH_2)_{10}$, $CH_2CH{=}CHCH_2CH{=}CH(CH_2)_7$, $(CH_2)_2CH{=}CHCH_2CH{=}CH(CH_2)_7$, $(CH_2)_3CH{=}CHCH_2CH{=}CH(CH_2)_7$, $(CH_2)_4CH{=}CHCH_2CH{=}CH(CH_2)_7$, $(CH_2)_5CH{=}CHCH_2CH{=}CH(CH_2)_7$, $(CH_2)_6CH{=}CHCH_2CH{=}CH(CH_2)_7$, $(CH_2)_7CH{=}CHCH_2CH{=}CH(CH_2)_7$, $(CH_2)_8CH{=}CHCH_2CH{=}CH(CH_2)_7$.

4. The compound according to claim 1, wherein

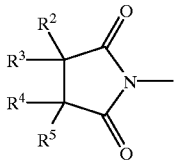

is a radical of the formula

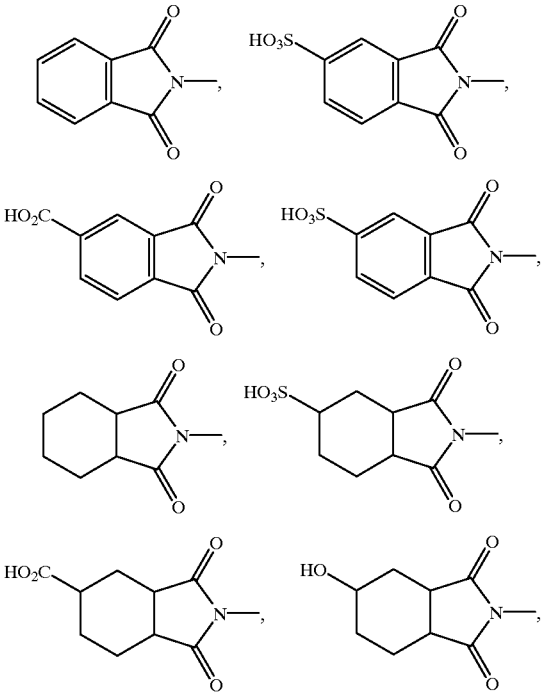

-continued

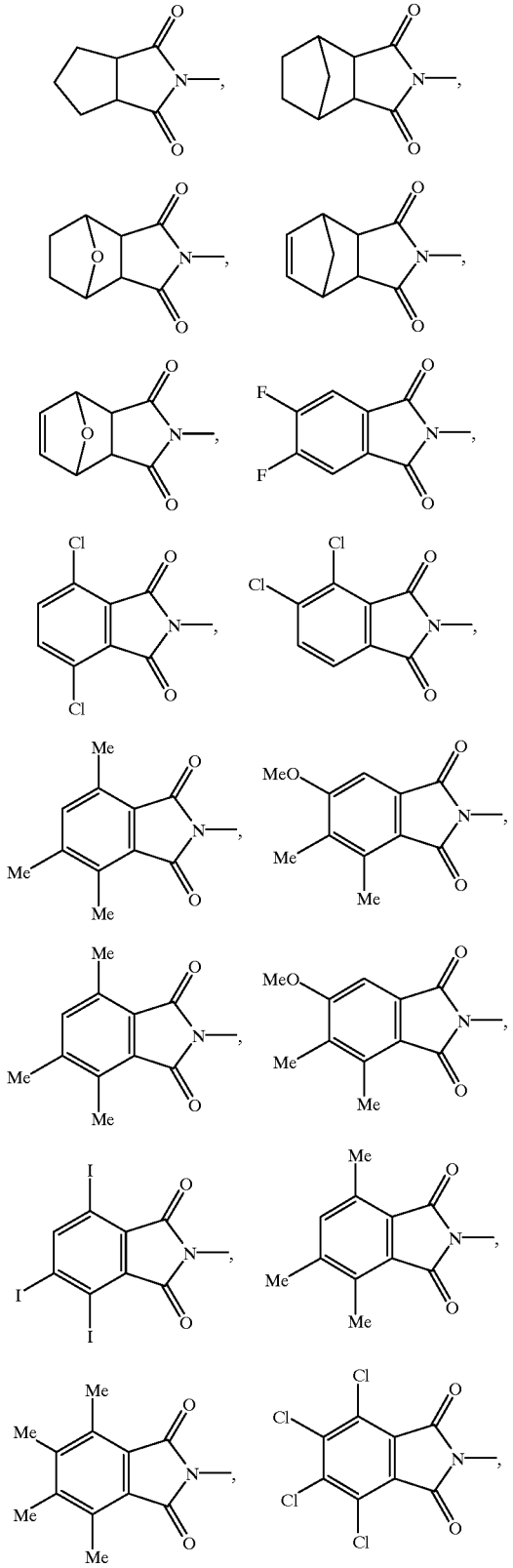

-continued

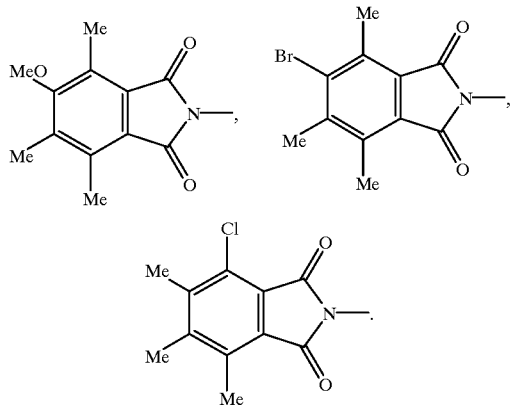

5. The compound according to claim 1, which is an alkali metal or alkaline earth metal salt.

6. The compound according to claim 1, which is N-(15-carboxypentadecanoyloxy)phthalimide.

7. The compound according to claim 1, which is N-(15-carboxypentadecanoyloxy)tetramethylphthalimide.

8. The compound according to claim 1, which is N-(15-carboxypentadecanoyloxy)-5-norbornene-2,3-dicarboximide.

9. A compound of the formula

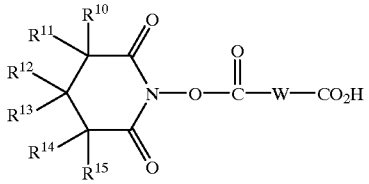

or a salt thereof, wherein W is a divalent long chain hydrocarbon radical having from 8 to 28 principal chain atoms; and wherein each of $R^{10}$, $R^{11}$, $R^{12}$, $R^{13}$, $R^{14}$ and $R^{15}$, which can be the same or different, is a hydrogen atom; an alkyl radical; an aryl radical; an aralkyl radical; an —$SO_3H$ group; a radical of the formula —$OH^6$ wherein $R^6$ is selected from the group consisting of a hydrogen atom, an alkyl radical, an aryl radical, an aralkyl radical and an acyl radical; a radical of the formula —$NR^7R^8$ wherein each of $R^7$ and $R^8$, which can be the same or different, is selected from the group consisting of an alkyl radical, an aryl radical, an aralkyl radical and an acyl radical; or a radical of the formula —$CO_2R^9$ wherein $R^9$ is selected from the group consisting of a hydrogen atom, an alkyl radical, an aryl radical or an aralkyl radical.

10. The compound according to claim 9, wherein the divalent hydrocarbon radical W has from 10 to 20 principal chain atoms.

11. The compound according to claim 10, wherein W is a divalent radical of the formula $(CH_2)_{10}$, $(CH_2)_{11}$, [$(CH_2)_{12}(CH_2)_{13}(CH_2)_{14}$,] $(CH_2)_{12}$, $(CH_2)_{13}$, $(CH_2)_{14}$, $(CH_2)_{15}$, $(CH_2)_{16}$, $(CH_2)_{17}$, $(CH_2)_{18}$, $(CH_2)_{19}$, $(CH_2)_{20}$, $CH_2CH{=}CH(CH_2)_7$, $(CH_2)_2CH{=}CH(CH_2)_7$, $(CH_2)_3CH{=}CH(CH_2)_7$, $(CH_2)_4CH{=}CH(CH_2)_7$, $(CH_2)_5CH{=}CH(CH_2)_7$, $(CH_2)_6CH{=}CH(CH_2)_7$, $(CH_2)_7CH{=}CH(CH_2)_7$, $(CH_2)_8CH{=}CH(CH_2)_7$, $(CH_2)_9CH{=}CH(CH_2)_7$, $(CH_2)_{10}CH{=}CH(CH_2)_7$, $(CH_2)_{11}CH{=}CH(CH_2)_7$, $(CH_2)_8CH{=}CHCH_2$, $(CH_2)_8CH{=}CH(CH_2)_2$, $(CH_2)_8CH{=}CH(CH_2)_3$, $(CH_2)_8CH{=}CH(CH_2)_4$, $(CH_2)_8CH{=}CH(CH_2)_5$, $(CH_2)_8CH{=}CH(CH_2)_6$, $(CH_2)_8CH{=}CH(CH_2)_8$, $(CH_2)_8CH{=}CH(CH_2)_9$, $(CH_2)_8CH{=}CH(CH_2)_{10}$, $CH_2CH{=}CHCH_2CH{=}CH(CH_2)_7$, $(CH_2)_2CH{=}CHCH_2CH{=}CH(CH_2)_7$, [$(CH_2)_3CH{=}CHCH_2CH{=}(CH_2)_7$,] $(CH_2)_3CH{=}CHCH_2CH{=}CH(CH_2)_7$, $(CH_2)_4CH{=}CHCH_2CH{=}CH(CH_2)_7$, $(CH_2)_5CH{=}CHCH_2CH{=}CH(CH_2)_7$, $(CH_2)_6CH{=}CHCH_2CH{=}CH(CH_2)_7$, $(CH_2)_7CH{=}CHCH_2CH{=}CH(CH_2)_7$, or $(CH_2)_8CH{=}CHCH_2CH{=}CH(CH_2)_7$.

12. The compound according to claim 9, wherein each of $R^{10}$, $R^{11}$, $R^{12}$, $R^{13}$, $R^{14}$ and $R^{15}$, which can be the same or different, is hydrogen, methyl, ethyl, propyl, isopropyl, octadecyl, phenyl, p-bromophenyl, benzyl, p-methoxybenzyl, —$SO_3H$, hydroxy, methoxy, ethoxy, propoxy, isopropoxy, phenoxy, p-bromophenoxy, benzyloxy, p-methoxybenzyloxy, acetoxy or benzoyloxy; or a radical of the formula —$NR^7R^8$ selected from the group consisting of dimethylamino, diethylamino, N-methylacetamido and N-methylbenzamido; or a radical of the formula —$CO_2R^9$ selected from the group consisting of carboxyl, methoxycarbonyl, ethoxycarbonyl, propoxycarbonyl, isopropoxycarbonyl, phenoxycarbonyl and p-bromophenoxycarbonyl.

13. The compound according to claim 9, which is an alkali metal or alkaline earth metal salt.

14. The compound according to claim 9, which is N-(15-carboxypentadecanoyloxy)glutarimide.

15. A compound of the formula

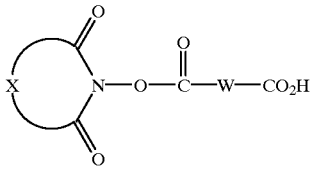

or a salt thereof, wherein W is a divalent long chain hydrocarbon radical interrupted by one or more groups each independently selected from the group consisting of an oxygen atom, a sulfur atom and an —$N(R^1)$— group wherein $R^1$ is lower alkyl, said radical W having from 8 to 28 principal chain atoms; and

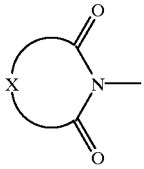

is a radical of the formula

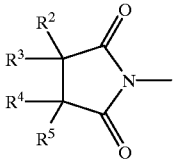

or

-continued

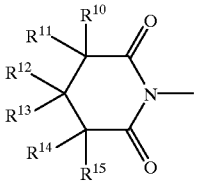

wherein each of $R^2$, $R^3$, $R^4$ and $R^5$, which can be the same or different, is a hydrogen atom; an alkyl radical; an aryl radical; an aralkyl radical; an $—SO_3H$ group; a radical of the formula $—OR^6$ wherein $R^6$ is selected from the group consisting of a hydrogen atom, an alkyl radical, an aryl radical, an aralkyl radical and an acyl radical; a radical of the formula $—NR^7R^8$ wherein each of $R^7$ and $R^8$, which can be the same or different, is selected from the group consisting of an alkyl radical, an aryl radical, an aralkyl radical and acyl radical; or a radical of the formula $—CO_2R^9$ wherein $R^9$ is selected from the group consisting of a hydrogen atom, an alkyl radical, an aryl radical and an aralkyl radical; or $R^2$, $R^3$, $R^4$ and $R^5$ can, in combination with the carbon atoms to which they bond, form a benzene, cyclohexane, cyclopentane, bicyclo [2.2.1]heptane, bicyclo[2.2.1]hepta-2-ene, 7-oxabicyclo[2.2.1]heptane or 7-oxabicyclo[2.2.1] hepta-2-ene ring system which is optionally substituted by $—SO_3H$, $—CO_2H$, —OH, F, Cl, Br, I, $—CH_3$ or $—OCH_3$; or $R^2$ and $R^3$ and/or $R^4$ and $R^5$, in combination, can be a methylene or isopropylidene group; and each of $R^{10}$, $R^{11}$, $R^{12}$, $R^{13}$, $R^{14}$ and $R^{15}$, which can be the same or different, is a hydrogen atom; an alkyl radical; an aryl radical; an aralkyl radical; an $—SO_3H$ group; a radical of the formula $—OR^6$ wherein $R^6$ is selected from the group consisting of a hydrogen atom, an alkyl radical, an aryl radical, an aralkyl radical and an acyl radical; a radical of the formula $—NR^7R^8$ wherein each of $R^7$ and $R^8$, which can be the same or different, is selected from the group consisting of an alkyl radical, an aryl radical, an aralkyl radical and an acyl radical; or a radical of the formula $—CO_2R^9$ wherein $R^9$ is selected from the group consisting of a hydrogen atom, an alkyl radical, an aryl radical or an aralkyl radical.

16. The compound according to claim 15, wherein the divalent hydrocarbon radical W has from 10 to 20 principal chain atoms.

17. The compound according to claim 15, wherein $R^1$ is methyl, ethyl, propyl or isopropyl.

18. The compound according to claim 16, wherein W is a divalent radical of the formula $(CH_2)_2—O—(CH_2)_7$, $(CH_2)_2—O—(CH_2)_8$, $(CH_2)_2—O—(CH_2)_9$, $(CH_2)_2—O—(CH_2)_{10}$, $(CH_2)_2—O—(CH_2)_{11}$, $(CH_2)_2—O—(CH_2)_{12}$, $(CH_2)_2—O—(CH_2)_{13}$, $(CH_2)_2—O—(CH_2)_{14}$, $(CH_2)_2—O—(CH_2)_{15}$, $(CH_2)_2—O—(CH_2)_{16}$, $(CH_2)_2—O—(CH_2)_{17}$, $(CH_2)_4—O—(CH_2)_5$, $(CH_2)_4—O—(CH_2)_6$, $(CH_2)_4—O—(CH_2)_7$, [$(CH_2)_4—O—$,$(CH_2)_8(CH_2)_4—O—(CH_2)_9$,] $(CH_2)_3—O—(CH_2)_8$, $(CH_2)_4—O—(CH_2)_9$, $(CH_2)_4—O—(CH_2)_{10}$, $(CH_2)_4—O—(CH_2)_{11}$, $(CH_2)_4—O—(CH_2)_{12}$, $(CH_2)_4—O—(CH_2)_{13}$, $(CH_2)_4—O—(CH_2)_{14}$, $(CH_2)_4—O—(CH_2)_{15}$, $(CH_2)_6—O—(CH_2)_3$, $(CH_2)_6—O—(CH_2)_4$, $(CH_2)_6—O—(CH_2)_5$, $(CH_2)_6—O—(CH_2)_6$, $(CH_2)_6—O—(CH_2)_7$, $(CH_2)_6—O—(CH_2)_8$, $(CH_2)_6—O—(CH_2)_9$, $(CH_2)_6—O—(CH_2)_{10}$, $(CH_2)_6—O—(CH_2)_{11}$, $(CH_2)_6—O—(CH_2)_{12}$, $(CH_2)_6—O—(CH_2)_{13}$, $(CH_2)_8—O—CH_2$, $(CH_2)_8—O—(CH_2)_2$, $(CH_2)_8—O—(CH_2)_3$, $(CH_2)_8—O—(CH_2)_4$, $(CH_2)_8—O—(CH_2)_5$, $(CH_2)_8—O—(CH_2)_6$, $(CH_2)_8—O—(CH_2)_7$, $(CH_2)_8—O—(CH_2)_8$, $(CH_2)_8—O—(CH_2)_9$, $(CH_2)_8—O—(CH_2)_{10}$, $(CH_2)_8—O—(CH_2)_{11}$, $(CH_2)_{10}—O—CH_2$, $(CH_2)_{10}—O—(CH_2)_2$, $(CH_2)_{10}—O—(CH_2)_3$, $(CH_2)_{10}—O—(CH_2)_4$, $(CH_2)_{10}—O—(CH_2)_5$, $(CH_2)_{10}—O—(CH_2)_6$, $(CH_2)_{10}—O—(CH_2)_7$, $(CH_2)_{10}—O—(CH_2)_8$, $(CH_2)_{10}—O—(CH_2)_9$, $(CH_2)_{12}—O—CH_2$, $(CH_2)_{12}—O—(CH_2)_2$, $(CH_2)_{12}—O—(CH_2)_3$, $(CH_2)_{12}—O—(CH_2)_4$, $(CH_2)_{12}—O—(CH_2)_5$, $(CH_2)_{12}—O—(CH_2)_6$, $(CH_2)_{12}—O—(CH_2)_7$, $CH_2—O—(CH_2)_5CH═CH(CH_2)_7$, $(CH_2)_2—O—(CH_2)_5CH═CH(CH_2)_7$, $(CH_2)_3—O—(CH_2)_5CH═CH(CH_2)_7$, $(CH_2)_4—O—(CH_2)_5CH═CH(CH_2)_7$, or $(CH_2)_5—O—(CH_2)_5CH═CH(CH_2)_7$.

19. The compound according to claim 16, wherein W is a divalent radical of the formula $(CH_2)_2—S—(CH_2)_7$, $(CH_2)_2—S—(CH_2)_8$, $(CH_2)_2—S—(CH_2)_9$, $(CH_2)_2—S—(CH_2)_{10}$, $(CH_2)_2—S—(CH_2)_{11}$, $(CH_2)_2—S—(CH_2)_{12}$, $(CH_2)_2—S—(CH_2)_{13}$, $(CH_2)_2—S—(CH_2)_{14}$, $(CH_2)_2—S—(CH_2)_{15}$, $(CH_2)_2—S—(CH_2)_{16}$, $(CH_2)_2—S—(CH_2)_{17}$, $(CH_2)_4—S—(CH_2)_5$, $(CH_2)_4—S—(CH_2)_6$, $(CH_2)_4—S—(CH_2)_7$, $(CH_2)_4—S—(CH_2)_8$, $(CH_2)_4—S—(CH_2)_9$, $(CH_2)_4—S—(CH_2)_{10}$, $(CH_2)_4—S—(CH_2)_{11}$, $(CH_2)_4—S—(CH_2)_{12}$, $(CH_2)_4—S—(CH_2)_{13}$, $(CH_2)_4—S—(CH_2)_{14}$, $(CH_2)_4—S—(CH_2)_{15}$, $(CH_2)_6—S—(CH_2)_3$, $(CH_2)_6—S—(CH_2)_4$, $(CH_2)_6—S—(CH_2)_5$, $(CH_2)_6—S—(CH_2)_6$, $(CH_2)_6—S—(CH_2)_7$, $(CH_2)_6—S—(CH_2)_8$, $(CH_2)_6—S—(CH_2)_9$, $(CH_2)_6—S—(CH_2)_{10}$, $(CH_2)_6—S—(CH_2)_{11}$, $(CH_2)_6—S—(CH_2)_{12}$, $(CH_2)_6—S—(CH_2)_{13}$, $(CH_2)_8—S—CH_2$, $(CH_2)_8—S—(CH_2)_2$, $(CH_2)_8—S—(CH_2)_3$, $(CH_2)_8—S—(CH_2)_4$, $(CH_2)_8—S—(CH_2)_5$, $(CH_2)_8—S—(CH_2)_6$, $(CH_2)_8—S—(CH_2)_7$, $(CH_2)_8—S—(CH_2)_8$, $(CH_2)_8—S—(CH_2)_9$, $(CH_2)_8—S—(CH_2)_{10}$, $(CH_2)_8—S—(CH_2)_{11}$, $(CH_2)_{10}—S—CH_2$, $(CH_2)_{10}—S—(CH_2)_2$, $(CH_2)_{10}—S—(CH_2)_3$, $(CH_2)_{10}—S—(CH_2)_4$, $(CH_2)_{10}—S—(CH_2)_5$, $(CH_2)_{10}—S—(CH_2)_6$, $(CH_2)_{10}—S—(CH_2)_7$, $(CH_2)_{10}—S—(CH_2)_8$, [$(CH_2)_{10}—S—(CH_2)_9$),] $(CH_2)_{10}—S—(CH_2)_9$, $(CH_2)_{12}—S—CH_2$, $(CH_2)_{12}—S—(CH_2)_2$, $(CH_2)_{12}—S—(CH_2)_3$, $(CH_2)_{12}—S—(CH_2)_4$, $(CH_2)_{12}—S—(CH_2)_5$, $(CH_2)_{12}—S—(CH_2)_6$, or $(CH_2)_{12}—S—(CH_2)_7$.

20. The compound according to claim 16, wherein W is a divalent radical of the formula $(CH_2)_2—N(CH_3)—(CH_2)_7$, $(CH_2)_2—N(CH_3)—(CH_2)_8$, $(CH_2)_2—N(CH_3)—(CH_2)_9$, $(CH_2)_2—N(CH_3)—(CH_2)_{10}$, $(CH_2)_2—N(CH_3)—(CH_2)_{11}$, $(CH_2)_2—N(CH_3)—(CH_2)_{12}$, $(CH_2)_2—N(CH_3)—(CH_2)_{13}$, $(CH_2)_2—N(CH_3)—(CH_2)_{14}$, $(CH_2)_2—N(CH_3)—(CH_2)_{15}$, $(CH_2)_2—N(CH_3)—(CH_2)_{16}$, $(CH_2)_2—N(CH_3)—(CH_2)_{17}$, $(CH_2)_4—N(CH_3)—(CH_2)_5$, $(CH_2)_4—N(CH_3)—(CH_2)_6$, $(CH_2)_4—N(CH_3)—(CH_2)_7$, $(CH_2)_4—N(CH_3)—(CH_2)_8$, $(CH_2)_4—N(CH_3)—(CH_2)_9$, $(CH_2)_4—N(CH_3)—(CH_2)_{10}$, $(CH_2)_4—N(CH_3)—(CH_2)_{11}$, $(CH_2)_4—N(CH_3)—(CH_2)_{12}$, $(CH_2)_4—N(CH_3)—(CH_2)_{13}$, $(CH_2)_4—N(CH_3)—(CH_2)_{14}$, $(CH_2)_4—N(CH_3)—(CH_2)_{15}$, $(CH_2)_6—N(CH_3)—(CH_2)_3$, $(CH_2)_6—N(CH_3)—(CH_2)_4$, $(CH_2)_6—N(CH_3)—(CH_2)_5$, $(CH_2)_6—N(CH_3)—(CH_2)_6$, $(CH_2)_6—N(CH_3)—(CH_2)_7$, $(CH_2)_6—N(CH_3)—(CH_2)_8$, $(CH_2)_6—N(CH_3)—(CH_2)_9$, $(CH_2)_6—N(CH_3)—(CH_2)_{10}$, $(CH_2)_6—N(CH_3)—(CH_2)_{11}$, $(CH_2)_6—N(CH_3)—(CH_2)_{12}$, $(CH_2)_6—N(CH_3)—(CH_2)_{13}$, $(CH_2)_2—N(C_2H_5)—(CH_2)_7$, $(CH_2)_2—N(C_2H_5)—(CH_2)_8$, $(CH_2)_2—N(C_2H_5)—(CH_2)_9$, $(CH_2)_2—N(C_2H_5)—(CH_2)_{10}$, $(CH_2)_2—N(C_2H_5)—(CH_2)_{11}$, $(CH_2)_2—N(C_2H_5)—(CH_2)_{12}$, $(CH_2)_2—N(C_2H_5)—(CH_2)_{13}$, $(CH_2)_2—N(C_2H_5)—(CH_2)_{14}$, $(CH_2)_2—N(C_2H_5)—(CH_2)_{15}$, $(CH_2)_2—N(C_2H_5)—(CH_2)_{16}$, $(CH_2)_2—N(C_2H_5)—(CH_2)_{17}$, $(CH_2)_4—N(C_2H_5)—(CH_2)_5$, $(CH_2)_4—N(C_2H_5)—(CH_2)_6$, $(CH_2)_4—N(C_2H_5)—(CH_2)_7$, $(CH_2)_4—N(C_2H_5)—(CH_2)_8$, $(CH_2)_4—N(C_2H_5)—(CH_2)_9$, $(CH_2)_4—N(C_2H_5)—(CH_2)_{10}$, $(CH_2)_4—N(C_2H_5)—(CH_2)_{11}$, $(CH_2)_4—N(C_2H_5)—(CH_2)_{12}$, $(CH_2)_4—N(C_2H_5)—(CH_2)_{13}$, $(CH_2)_4—N(C_2H_5)—(CH_2)_{14}$, $(CH_2)_4—N(C_2H_5)—(CH_2)_{15}$, $(CH_2)_6—N(C_2H_5)—(CH_2)_3$, $(CH_2)_6—N(C_2H_5)—(CH_2)_4$, $(CH_2)_6—N(C_2H_5)—(CH_2)_5$, $(CH_2)_6—N(C_2H_5)—(CH_2)_6$, $(CH_2)_6—N(C_2H_5)—(CH_2)_7$, $(CH_2)_6—N(C_2H_5)—(CH_2)_8$, $(CH_2)_6—N(C_2H_5)—(CH_2)_9$, $(CH_2)_6—N(C_2H_5)—(CH_2)_{10}$, $(CH_2)_6—N(C_2H_5)—(CH_2)_{11}$, $(CH_2)_6—N(C_2H_5)—(CH_2)_{12}$, or $(CH_2)_6—N(C_2H_5)—(CH_2)_{13}$.

21. The compound according to claim 16, wherein W is a divalent radical of the formula $(CH_2)_2$—O—$(CH_2)_2$—O—$(CH_2)_4$, $(CH_2)_2$—O—$(CH_2)_2$—O—$(CH_2)_5$, $(CH_2)_2$—O—$(CH_2)_2$—O—$(CH_2)_6$, $(CH_2)_2$—O—$(CH_2)_2$—O—$(CH_2)_7$, $(CH_2)_2$—O—$(CH_2)_2$—O—$(CH_2)_8$, $(CH_2)_2$—O—$(CH_2)_2$—O—$(CH_2)_9$, $(CH_2)_2$—O—$(CH_2)_2$—O—$(CH_2)_{10}$, $(CH_2)_2$—O—$(CH_2)_2$—O—$(CH_2)_{11}$, $(CH_2)_2$—O—$(CH_2)_2$—O—$(CH_2)_{12}$, $(CH_2)_2$—O—$(CH_2)_2$—O—$(CH_2)_{13}$, $(CH_2)_2$—O—$(CH_2)_2$—O—$(CH_2)_{14}$, $(CH_2)_4$—O—$(CH_2)_2$—O—$(CH_2)_2$, $(CH_2)_4$—O—$(CH_2)_2$—O—$(CH_2)_3$, $(CH_2)_4$—O—$(CH_2)_2$—O—$(CH_2)_4$, $(CH_2)_4$—O—$(CH_2)_2$—O—$(CH_2)_5$, $(CH_2)_4$—O—$(CH_2)_2$—O—$(CH_2)_6$, $(CH_2)_4$—O—$(CH_2)_2$—O—$(CH_2)_7$, $(CH_2)_4$—O—$(CH_2)_2$—O—$(CH_2)_8$, $(CH_2)_4$—O—$(CH_2)_2$—O—$(CH_2)_9$, $(CH_2)_4$—O—$(CH_2)_2$—O—$(CH_2)_{10}$, $(CH_2)_4$—O—$(CH_2)_2$—O—$(CH_2)_{11}$, or $(CH_2)_4$—O—$(CH_2)_2$—O—$(CH_2)_{12}$.

22. The compound according to claim 16, wherein W is a divalent radical of the formula $(CH_2)_2$—S—S—$(CH_2)_7$, $(CH_2)_2$—S—S—$(CH_2)_9$, $(CH_2)_2$—S—S—$(CH_2)_{11}$, $(CH_2)_2$—S—S—$(CH_2)_{13}$, $(CH_2)_2$—S—S—$(CH_2)_{15}$, $(CH_2)_4$—S—S—$(CH_2)_5$, $(CH_2)_4$—S—S—$(CH_2)_7$, $(CH_2)_4$—S—S—$(CH_2)_9$, $(CH_2)_4$—S—S—$(CH_2)_{11}$, $(CH_2)_4$—S—S—$(CH_2)_{13}$, $(CH_2)_6$—S—S—$(CH_2)_3$, $(CH_2)_6$—S—S—$(CH_2)_5$, $(CH_2)_6$—S—S—$(CH_2)_7$, $(CH_2)_6$—S—S—$(CH_2)_9$, $(CH_2)_6$—S—S—$(CH_2)_{11}$, $(CH_2)_8$—S—S—$CH_2$, $(CH_2)_8$—S—S—$(CH_2)_3$, $(CH_2)_8$—S—S—$(CH_2)_5$, $(CH_2)_8$—S—S—$(CH_2)_7$, or $(CH_2)_8$—S—S—$(CH_2)_9$.

23. The compound according to claim 15, wherein

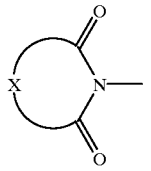

is a radical of the formula

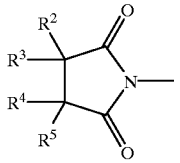

wherein each of $R^2$, $R^3$, $R^4$ and $R^5$, which can be the same or different, is a hydrogen atom; an alkyl radical; an aryl radical; an aralkyl radical; an —$SO_3H$ group; a radical of the formula —$OR^6$ wherein $R^6$ is selected from the group consisting of a hydrogen atom, an alkyl radical, an aryl radical, an aralkyl radical and an acyl radical; a radical of the formula —$NR^7R^8$ wherein each of $R^7$ and $R^8$, which can be the same or different, is selected from the group consisting of an alkyl radical, an aryl radical, an aralkyl radical and acyl radical; or a radical of the formula —$CO_2R^9$ wherein $R^9$ is selected from the group consisting of a hydrogen atom, an alkyl radical, an aryl radical and an aralkyl radical; or $R^2$, $R^3$, $R^4$ and $R^5$ can, in combination with the carbon atoms to which they bond, form a benzene, cyclohexane, cyclopentane, bicyclo [2.2.1]heptane, bicyclo[2.2.1]hepta-2-ene, 7-oxabicyclo[2.2.1]heptane or 7-oxabicyclo[2.2.1] hepta-2-ene ring system which is optionally substituted by —$SO_3H$, —$CO_2H$, —OH, F, Cl, Br, I, —$CH_3$ or —$OCH_3$; or $R^2$ and $R^3$ and/or $R^4$ and $R^5$, in combination, can be a methylene or isopropylidene group.

24. The compound according to claim 23, wherein $R^2$, $R^3$, $R^4$ and $R^5$, in combination with the carbon atoms to which they bond, form a benzene, cyclohexane, cyclopentane, bicyclo[2.2.1]heptane, bicyclo[2.2.1]hepta-2-ene, 7-oxabicyclo[2.2.1]heptane or 7-oxabicyclo[2.2.1]hepta-2-ene ring system which is optionally substituted by —$SO_3H$, —$CO_2H$, —OH, F, Cl, Br, I, —$CH_3$ or —$OCH_3$.

25. The compound according to claim 23, wherein each of $R^2$, $R^3$, $R^4$ and $R^5$, which can be the same or different, is hydrogen, methyl, ethyl, propyl, isopropyl, octadecyl, phenyl, p-bromophenyl, benzyl, p-methoxybenzyl, —$SO_3H$, hydroxy, methoxy, ethoxy, propoxy, isopropoxy, phenoxy, p-bromophenoxy, benzyloxy, p-methoxybenzyloxy, acetoxy or benzoyloxy; or a radical of the formula —$NR^7R^8$ selected from the group consisting of dimethylamino, diethylamino, N-methylacetamido and N-methylbenzamido; or a radical of the formula —$CO_2R^9$ selected from the group consisting of carboxyl, methoxycarbonyl, ethoxycarbonyl, propoxycarbonyl, isopropoxycarbonyl, phenoxycarbonyl and p-bromophenoxycarbonyl.

26. The compound according to claim 23, wherein $R^2$ and $R^3$ and/or $R^4$ and $R^5$, in combination, form a methylene or isopropylidene group.

27. The compound according to claim 26, wherein

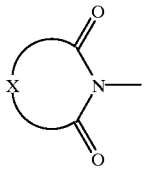

is a radical of the formula

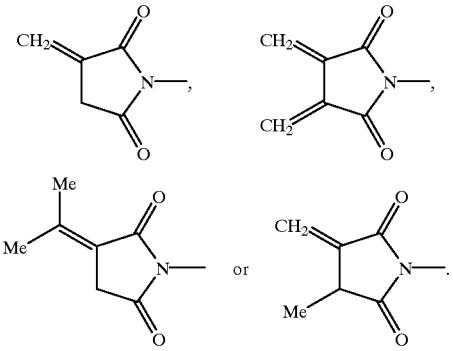

28. The compound according to claim 24, wherein

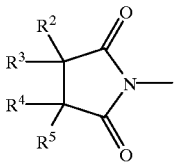

is a radical of the formula

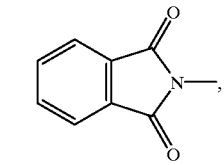

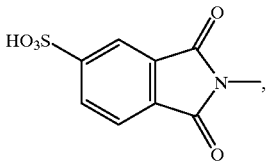

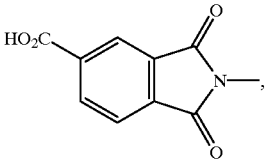

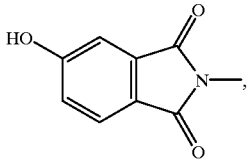

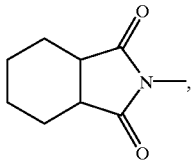

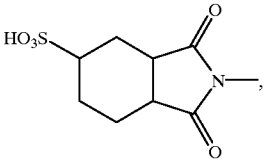

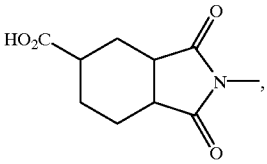

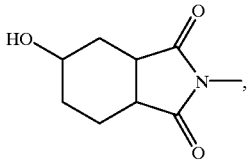

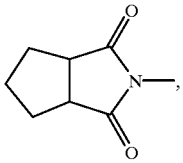

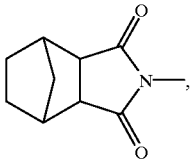

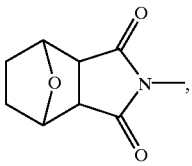

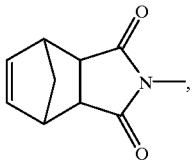

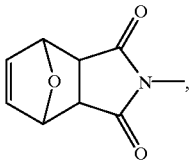

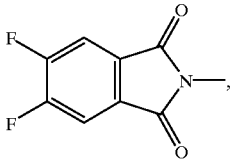

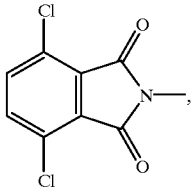

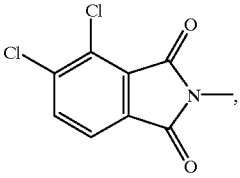

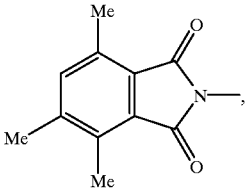

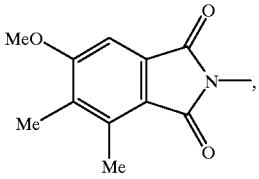

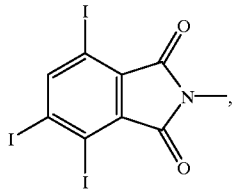

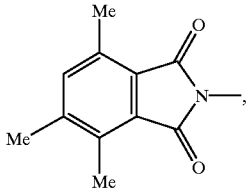

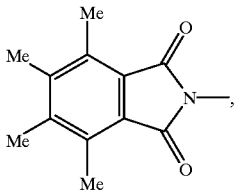

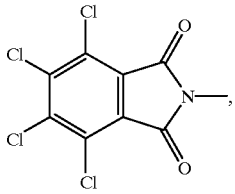

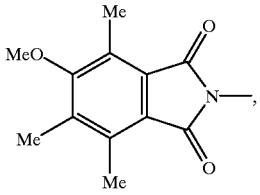

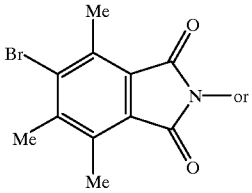

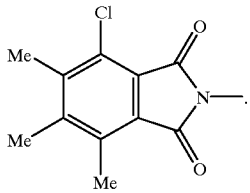

-continued

29. The compound according to claim 15, wherein

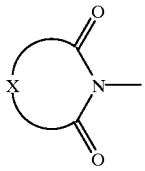

is a radical of the formula

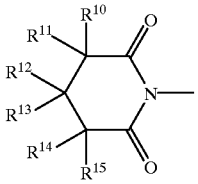

wherein each of $R^{10}$, $R^{11}$, $R^{12}$, $R^{13}$, $R^{14}$ and $R^{15}$, which can be the same or different, is a hydrogen atom; an alkyl radical; an aryl radical; an aralkyl radical; an —$SO_3H$ group; a radical of the formula —$OR^6$ wherein $R^6$ is selected from the group consisting of a hydrogen atom, an alkyl radical, an aryl radical, an aralkyl radical and an acyl radical; a radical of the formula —$NR^7R^8$ wherein each of $R^7$ and $R^8$, which can be the same or different, is selected from the group consisting of an alkyl radical, an aryl radical, an aralkyl radical and an acyl radical; or a radical of the formula —$CO_2R^9$ wherein $R^9$ is selected from the group consisting of a hydrogen atom, an alkyl radical, an aryl radical or an aralkyl radical.

30. The compound according to claim 29, wherein each of $R^{10}$, $R^{11}$, $R^{12}$, $R^{13}$, $R^{14}$ and $R^{15}$, which can be the same or different, is hydrogen, methyl, ethyl, propyl, isopropyl, octadecyl, phenyl, p-bromophenyl, benzyl, p-methoxybenzyl, —$SO_3H$, hydroxy, methoxy, ethoxy, propoxy, isopropoxy, phenoxy, p-bromophenoxy, benzyloxy, p-methoxybenzyloxy, acetoxy or benzoyloxy; or a radical of the formula —$NR^7R^8$ selected from the group consisting of dimethylamino, diethylamino, N-methylacetamido and N-methylbenzamido; or a radical of the formula —$CO_2R^9$ selected from the group consisting of carboxyl, methoxycarbonyl, ethoxycarbonyl, propoxycarbonyl, isopropoxycarbonyl, phenoxycarbonyl and p-bromophenoxycarbonyl.

31. The compound according to claim 15, which is an alkali metal or alkaline earth metal salt.

*32. A protein compound having the formula*

$$(protein)(Z)_n$$

*wherein (protein) represents a pharmacologically active protein having n amino radicals each derivable from an amino group by removal of one of its hydrogen atoms, and (Z) is a radical of a long chain carboxylic acid having the formula*

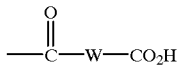

*wherein W is a divalent long chain hydrocarbon radical which is uninterrupted or interrupted by one or more groups each independently selected from the group consisting of an oxygen atom, a sulfur atom and an —N($R^1$) group wherein $R^1$ is lower alkyl, said radical W having from 8 to 28 principal chain atoms, each (Z) being derivable from a long chain dicarboxylic acid $HO_2C$—W—$CO_2H$ by removal of a hydroxyl group from one of its carbonyl groups, each (Z) being bonded to one of said n amino radicals in the protein, n being an average of the number of amide bonds between (Z) and (protein) and being a number from 1 to 8.*

*33. A protein compound according to claim 32, wherein the divalent radical W has from 10 to 20 principal chain atoms.*

*34. A protein compound according to claim 32, wherein $R^1$ is methyl, ethyl, propyl or isopropyl.*

*35. A protein compound according to claim 33, wherein W is a divalent radical of the formula* $(CH_2)_{10}$, $(CH_2)_{11}$, $(CH_2)_{13}$, $(CH_2)_{14}$, $(CH_2)_{15}$, $(CH_2)_{16}$, $(CH_2)_{17}$, $(CH_2)_{18}$, $(CH_2)_{19}$, $(CH_2)_{20}$, $CH_2CH$—$CH(CH_2)_7$, $(CH_2)_2CH$=$CH(CH_2)_7$, $(CH_2)_3CH$=$CH(CH_2)_7$, $(CH_2)_4CH$=$CH(CH_2)_7$, $(CH_2)_5CH$=$CH(CH_2)_7$, $(CH_2)_6CH$=$CH(CH_2)_7$, $(CH_2)_7CH$=$CH(CH_2)_7$, $(CH_2)_8CH$=$CH(CH_2)_7$, $(CH_2)_9CH$=$CH(CH_2)_7$, $(CH_2)_{10}CH$=$CH(CH_2)_7$, $(CH_2)_{11}CH$=$CH(CH_2)_7$, $(CH_2)_8CH$=$CHCH_2$, $(CH_2)_8CH$=$CH(CH_2)_2$, $(CH_2)_8CH$=$CH(CH_2)_3$, $(CH_2)_8CH$=$CH(CH_2)_4$, $(CH_2)_8CH$=$CH(CH_2)_5$, $(CH_2)_8CH$=$CH(CH_2)_6$, $(CH_2)_8CH$=$CH(CH_2)_8$, $(CH_2)_8CH$=$CH(CH_2)_9$, $(CH_2)_8CH$=$CH(CH_2)_{10}$, $CH_2CH$=$CHCH_2CH$=$CH(CH_2)_7$, $(CH_2)_2CH$=$CHCH_2CH$=$CH(CH_2)_7$, $(CH_2)_3CH$=$CHCH_2CH$=$CH(CH_2)_7$, $(CH_2)_4CH$=$CHCH_2CH$=$CH(CH_2)_7$, $(CH_2)_5CH$=$CHCH_2CH$=$CH(CH_2)_7$, $(CH_2)_6CH$=$CHCH_2CH$=$CH(CH_2)_7$, $(CH_2)_7CH$=$CHCH_2CH$=$CH(CH_2)_7$, *or* $(CH_2)_8CH$=$CHCH_2CH$=$CH(CH_2)_7$.

*36. A protein compound according to claim 35, wherein W is a divalent group of the formula* $(CH_2)_{12}$, $(CH_2)_{14}$, $(CH_2)_{16}$, $(CH_2)_{18}$ *or* $(CH_2)_{20}$.

*37. A protein compound according to claim 33, wherein W is a divalent radical of the formula* $(CH_2)_2$—O—$(CH_2)_7$, $(CH_2)_2$—O—$(CH_2)_8$, $(CH_2)_2$—O—$(CH_2)_9$, $(CH_2)_2$—O—$(CH_2)_{10}$, $(CH_2)_2$—O—$(CH_2)_{11}$, $(CH_2)_2$—O—$(CH_2)_{12}$, $(CH_2)_2$—O—$(CH_2)_{13}$, $(CH_2)_2$—O—$(CH_2)_{14}$, $(CH_2)_2$—O—$(CH_2)_{15}$, $(CH_2)_2$—O—$(CH_2)_{16}$, $(CH_2)_2$—O—$(CH_2)_{17}$, $(CH_2)_4$—O—$(CH_2)_5$, $(CH_2)_4$—O—$(CH_2)_6$, $(CH_2)_4$—O—$(CH_2)_7$, $(CH_2)_4$—O—$(CH_2)_8$, $(CH_2)_4$—O—$(CH_2)_9$, $(CH_2)_4$—O—$(CH_2)_{10}$, $(CH_2)_4$—O—$(CH_2)_{11}$, $(CH_2)_4$—O—$(CH_2)_{12}$, $(CH_2)_4$—O—$(CH_2)_{13}$, $(CH_2)_4$—O—$(CH_2)_{14}$, $(CH_2)_4$—O—$(CH_2)_{15}$, $(CH_2)_6$—O—$(CH_2)_3$, $(CH_2)_6$—O—$(CH_2)_4$, $(CH_2)_6$—O—$(CH_2)_5$, $(CH_2)_6$—O—$(CH_2)_6$, $(CH_2)_6$—O—$(CH_2)_7$, $(CH_2)_6$—O—$(CH_2)_8$, $(CH_2)_6$—O—$(CH_2)_9$, $(CH_2)_6$—O—$(CH_2)_{10}$, $(CH_2)_6$—O—$(CH_2)_{11}$, $(CH_2)_6$—O—$(CH_2)_{12}$, $(CH_2)_6$—O—$(CH_2)_{13}$, $(CH_2)_8$—O—$CH_2$, $(CH_2)_8$—O—$(CH_2)_2$, $(CH_2)_8$—O—$(CH_2)_3$, $(CH_2)_8$—O—$(CH_2)_4$, $(CH_2)_8$—O—$(CH_2)_5$, $(CH_2)_8$—O—$(CH_2)_6$, $(CH_2)_8$—O—$(CH_2)_7$, $(CH_2)_8$—O—$(CH_2)_8$, $(CH_2)_8$—O—$(CH_2)_9$, $(CH_2)_8$—O—$(CH_2)_{10}$, $(CH_2)_8$—O—$(CH_2)_{11}$, $(CH_2)_{10}$—O—$CH_2$, $(CH_2)_{10}$—O—$(CH_2)_2$, $(CH_2)_{10}$—O—$(CH_2)_3$, $(CH_2)_{10}$—O—$(CH_2)_4$, $(CH_2)_{10}$—O—$(CH_2)_5$, $(CH_2)_{10}$—O—$(CH_2)_6$, $(CH_2)_{10}$—O—$(CH_2)_7$, $(CH_2)_{10}$—O—$(CH_2)_8$, $(CH_2)_{10}$—O—$(CH_2)_9$, $(CH_2)_{12}$—O—$CH_2$, $(CH_2)_{12}$—O—$(CH_2)_2$, $(CH_2)_{12}$—O—$(CH_2)_3$, $(CH_2)_{12}$—O—$(CH_2)_4$, $(CH_2)_{12}$—O—$(CH_2)_5$, $(CH_2)_{12}$—O—$(CH_2)_6$, $(CH_2)_{12}$—O—$(CH_2)_7$, $CH_2$—O—$(CH_2)_5CH$=$CH(CH_2)_7$, $(CH_2)_2$—O—$(CH_2)_5CH$=$CH(CH_2)_7$, $(CH_2)_3$—O—$(CH_2)_5CH$=$CH(CH_2)_7$, $(CH_2)_4$—O—$(CH_2)_5CH$=$CH(CH_2)_7$, *or* $(CH_2)_5$—O—$(CH_2)_5CH$=$CH(CH_2)_7$.

*38. A protein compound according to claim 33, wherein W is a divalent radical of the formula* $(CH_2)_2$—S—$(CH_2)_7$, $(CH_2)_2$—S—$(CH_2)_8$, $(CH_2)_2$—S—$(CH_2)_9$, $(CH_2)_2$—S—$(CH_2)_{10}$, $(CH_2)_2$—S—$(CH_2)_{11}$, $(CH_2)_2$—S—$(CH_2)_{12}$, $(CH_2)_2$—S—$(CH_2)_{13}$, $(CH_2)_2$—S—$(CH_2)_{14}$, $(CH_2)_2$—S—$(CH_2)_{15}$, $(CH_2)_2$—S—$(CH_2)_{16}$, $(CH_2)_2$—S—$(CH_2)_{17}$, $(CH_2)_4$—S—$(CH_2)_5$, $(CH_2)_4$—S—$(CH_2)_6$, $(CH_2)_4$—S—$(CH_2)_7$, $(CH_2)_4$—S—$(CH_2)_8$, $(CH_2)_4$—S—$(CH_2)_9$, $(CH_2)_4$—S—$(CH_2)_{10}$, $(CH_2)_4$—S—$(CH_2)_{11}$, $(CH_2)_4$—S—$(CH_2)_{12}$, $(CH_2)_4$—S—$(CH_2)_{13}$, $(CH_2)_4$—S—$(CH_2)_{14}$, $(CH_2)_4$—S—$(CH_2)_{15}$, $(CH_2)_6$—S—$(CH_2)_3$, $(CH_2)_6$—S—$(CH_2)_4$, $(CH_2)_6$—S—$(CH_2)_5$, $(CH_2)_6$—S—$(CH_2)_6$, $(CH_2)_6$—S—$(CH_2)_7$, $(CH_2)_6$—S—$(CH_2)_8$, $(CH_2)_6$—S—$(CH_2)_9$, $(CH_2)_6$—S—$(CH_2)_{10}$, $(CH_2)_6$—S—$(CH_2)_{11}$, $(CH_2)_6$—S—$(CH_2)_{12}$, $(CH_2)_6$—S—$(CH_2)_{13}$, $(CH_2)_8$—S—$CH_2$, $(CH_2)_8$—S—$(CH_2)_2$, $(CH_2)_8$—S—$(CH_2)_3$, $(CH_2)_8$—S—$(CH_2)_4$, $(CH_2)_8$—S—$(CH_2)_5$, $(CH_2)_8$—S—$(CH_2)_6$, $(CH_2)_8$—S—$(CH_2)_7$, $(CH_2)_8$—S—$(CH_2)_8$, $(CH_2)_8$—S—$(CH_2)_9$, $(CH_2)_8$—S—$(CH_2)_{10}$, $(CH_2)_8$—S—$(CH_2)_{11}$, $(CH_2)_{10}$—S—$CH_2$, $(CH_2)_{10}$—S—$(CH_2)_2$, $(CH_2)_{10}$—S—$(CH_2)_3$, $(CH_2)_{10}$—S—$(CH_2)_4$, $(CH_2)_{10}$—S—$(CH_2)_5$, $(CH_2)_{10}$—S—$(CH_2)_6$, $(CH_2)_{10}$—S—$(CH_2)_7$, $(CH_2)_{10}$—S—$(CH_2)_8$, $(CH_2)_{10}$—S—$(CH_2)_9$, $(CH_2)_{12}$—S—$CH_2$, $(CH_2)_{12}$—S—$(CH_2)_2$, $(CH_2)_{12}$—S—$(CH_2)_3$, $(CH_2)_{12}$—S—$(CH_2)_4$, $(CH_2)_{12}$—S—$(CH_2)_5$, $(CH_2)_{12}$—S—$(CH_2)_6$, *or* $(CH_2)_{12}$—S—$(CH_2)_7$.

*39. A protein compound according to claim 33, wherein W is a divalent radical of the formula* $(CH_2)_2$—N($CH_3$)—$(CH_2)_7$, $(CH_2)_2$—N($CH_3$)—$(CH_2)_8$, $(CH_2)_2$—N($CH_3$)—$(CH_2)_9$, $(CH_2)_2$—N($CH_3$)—$(CH_2)_{10}$, $(CH_2)_2$—N($CH_3$)—$(CH_2)_{11}$, $(CH_2)_2$—N($CH_3$)—$(CH_2)_{12}$, $(CH_2)_2$—N($CH_3$)—$(CH_2)_{13}$, $(CH_2)_2$—N($CH_3$)—$(CH_2)_{14}$, $(CH_2)_2$—N($CH_3$)—$(CH_2)_{15}$, $(CH_2)_2$—N($CH_3$)—$(CH_2)_{16}$, $(CH_2)_2$—N($CH_3$)—$(CH_2)_{17}$, $(CH_2)_4$—N($CH_3$)—$(CH_2)_5$, $(CH_2)_4$—N($CH_3$)—$(CH_2)_6$, $(CH_2)_4$—N($CH_3$)—$(CH_2)_7$, $(CH_2)_4$—N($CH_3$)—$(CH_2)_8$, $(CH_2)_4$—N($CH_3$)—$(CH_2)_9$, $(CH_2)_4$—N($CH_3$)—$(CH_2)_{10}$, $(CH_2)_4$—N($CH_3$)—$(CH_2)_{11}$, $(CH_2)_4$—N($CH_3$)—$(CH_2)_{12}$, $(CH_2)_4$—N($CH_3$)—$(CH_2)_{13}$, $(CH_2)_4$—N($CH_3$)—$(CH_2)_{14}$, $(CH_2)_4$—N($CH_3$)—$(CH_2)_{15}$, $(CH_2)_6$—N($CH_3$)—

$(CH_2)_3$, $(CH_2)_6$—$N(CH_3)$—$(CH_2)_4$, $(CH_2)_6$—$N(CH_3)$—$(CH_2)_5$, $(CH_2)_6$—$N(CH_3)$—$(CH_2)_6$, $(CH_2)_6$—$N(CH_3)$—$(CH_2)_7$, $(CH_2)_6$—$N(CH_3)$—$(CH_2)_8$, $(CH_2)_6$—$N(CH_3)$—$(CH_2)_9$, $(CH_2)_6$—$N(CH_3)$—$(CH_2)_{10}$, $(CH_2)_6$—$N(CH_3)$—$(CH_2)_{11}$, $(CH_2)_6$—$N(CH_3)$—$(CH_2)_{12}$, $(CH_2)_6$—$N(CH_3)$—$(CH_2)_{13}$, $(CH_2)_2$—$N(C_2H_5)$—$(CH_2)_7$, $(CH_2)_2$—$N(C_2H_5)$—$(CH_2)_8$, $(CH_2)_2$—$N(C_2H_5)$—$(CH_2)_9$, $(CH_2)_2$—$N(C_2H_5)$—$(CH_2)_{10}$, $(CH_2)_2$—$N(C_2H_5)$—$(CH_2)_{11}$, $(CH_2)_2$—$N(C_2H_5)$—$(CH_2)_{12}$, $(CH_2)_2$—$N(C_2H_5)$—$(CH_2)_{13}$, $(CH_2)_2$—$N(C_2H_5)$—$(CH_2)_{14}$, $(CH_2)_2$—$N(C_2H_5)$—$(CH_2)_{15}$, $(CH_2)_2$—$N(C_2H_5)$—$(CH_2)_{16}$, $(CH_2)_2$—$N(C_2H_5)$—$(CH_2)_{17}$, $(CH_2)_4$—$N(C_2H_5)$—$(CH_2)_5$, $(CH_2)_4$—$N(C_2H_5)$—$(CH_2)_6$, $(CH_2)_4$—$N(C_2H_5)$—$(CH_2)_7$, $(CH_2)_4$—$N(C_2H_5)$—$(CH_2)_8$, $(CH_2)_4$—$N(C_2H_5)$—$(CH_2)_9$, $(CH_2)_4$—$N(C_2H_5)$—$(CH_2)_{10}$, $(CH_2)_4$—$N(C_2H_5)$—$(CH_2)_{11}$, $(CH_2)_4$—$N(C_2H_5)$—$(CH_2)_{12}$, $(CH_2)_4$—$N(C_2H_5)$—$(CH_2)_{13}$, $(CH_2)_4$—$N(C_2H_5)$—$(CH_2)_{14}$, $(CH_2)_4$—$N(C_2H_5)$—$(CH_2)_{15}$, $(CH_2)_6$—$N(C_2H_5)$—$(CH_2)_3$, $(CH_2)_6$—$N(C_2H_5)$—$(CH_2)_4$, $(CH_2)_6$—$N(C_2H_5)$—$(CH_2)_5$, $(CH_2)_6$—$N(C_2H_5)$—$(CH_2)_6$, $(CH_2)_6$—$N(C_2H_5)$—$(CH_2)_7$, $(CH_2)_6$—$N(C_2H_5)$—$(CH_2)_8$, $(CH_2)_6$—$N(C_2H_5)$—$(CH_2)_9$, $(CH_2)_6$—$N(C_2H_5)$—$(CH_2)_{10}$, $(CH_2)_6$—$N(C_2H_5)$—$(CH_2)_{11}$, $(CH_2)_6$—$N(C_2H_5)$—$(CH_2)_{12}$, *or* $(CH_2)_6$—$N(C_2H_5)$—$(CH_2)_{13}$.

*40. A protein compound according to claim 33, wherein W is a divalent radical of the formula* $(CH_2)_2$—$O$—$(CH_2)_2$—$O$—$(CH_2)_4$, $(CH_2)_2$—$O$—$(CH_2)_2$—$O$—$(CH_2)_5$, $(CH_2)_2$—$O$—$(CH_2)_2$—$O$—$(CH_2)_6$, $(CH_2)_2$—$O$—$(CH_2)_2$—$O$—$(CH_2)_7$, $(CH_2)_2$—$O$—$(CH_2)_2$—$O$—$(CH_2)_8$, $(CH_2)_2$—$O$—$(CH_2)_2$—$O$—$(CH_2)_9$, $(CH_2)_2$—$O$—$(CH_2)_2$—$O$—$(CH_2)_{10}$, $(CH_2)_2$—$O$—$(CH_2)_2$—$O$—$(CH_2)_{11}$, $(CH_2)_2$—$O$—$(CH_2)_2$—$O$—$(CH_2)_{12}$, $(CH_2)_2$—$O$—$(CH_2)_2$—$O$—$(CH_2)_{13}$, $(CH_2)_2$—$O$—$(CH_2)_2$—$O$—$(CH_2)_{14}$, $(CH_2)_4$—$O$—$(CH_2)_2$—$O$—$(CH_2)_2$, $(CH_2)_4$—$O$—$(CH_2)_2$—$O$—$(CH_2)_3$, $(CH_2)_4$—$O$—$(CH_2)_2$—$O$—$(CH_2)_4$, $(CH_2)_4$—$O$—$(CH_2)_2$—$O$—$(CH_2)_5$, $(CH_2)_4$—$O$—$(CH_2)_2$—$O$—$(CH_2)_6$, $(CH_2)_4$—$O$—$(CH_2)_2$—$O$—$(CH_2)_7$, $(CH_2)_4$—$O$—$(CH_2)_2$—$O$—$(CH_2)_8$, $(CH_2)_4$—$O$—$(CH_2)_2$—$O$—$(CH_2)_9$, $(CH_2)_4$—$O$—$(CH_2)_2$—$O$—$(CH_2)_{10}$, $(CH_2)_4$—$O$—$(CH_2)_2$—$O$—$(CH_2)_{11}$, *or* $(CH_2)_4$—$O$—$(CH_2)_2$—$O$—$(CH_2)_{12}$.

*41. A protein compound according to claim 33, wherein W is a divalent radical of the formula* $(CH_2)_2$—$S$—$S$—$(CH_2)_7$, $(CH_2)_2$—$S$—$S$—$(CH_2)_9$, $(CH_2)_2$—$S$—$S$—$(CH_2)_{11}$, $(CH_2)_2$—$S$—$S$—$(CH_2)_{13}$, $(CH_2)_2$—$S$—$S$—$(CH_2)_{15}$, $(CH_2)_4$—$S$—$S$—$(CH_2)_5$, $(CH_2)_4$—$S$—$S$—$(CH_2)_7$, $(CH_2)_4$—$S$—$S$—$(CH_2)_9$, $(CH_2)_4$—$S$—$S$—$(CH_2)_{11}$, $(CH_2)_4$—$S$—$S$—$(CH_2)_{13}$, $(CH_2)_6$—$S$—$S$—$(CH_2)_3$, $(CH_2)_6$—$S$—$S$—$(CH_2)_5$, $(CH_2)_6$—$S$—$S$—$(CH_2)_7$, $(CH_2)_6$—$S$—$S$—$(CH_2)_9$, $(CH_2)_6$—$S$—$S$—$(CH_2)_{11}$, $(CH_2)_8$—$S$—$S$—$CH_2$, $(CH_2)_8$—$S$—$S$—$(CH_2)_3$, $(CH_2)_8$—$S$—$S$—$(CH_2)_5$, $(CH_2)_8$—$S$—$S$—$(CH_2)_7$, *or* $(CH_2)_8$—$S$—$S$—$(CH_2)_9$.

*42. A protein compound according to claim 32 wherein said pharmacologically active protein is asparaginase arginase, interleukin-1, interleukin-2, interleukin-3, interleukin-4, interleukin-5, interleukin-6, interleukin-7, interleukin-8, urokinase, prourokinase, streptokinase, tissue plasminogen activator, β-glucosidase, β-glucuronidase, α-galactosidase deaminase, uricase, superoxide dismutase, insulin, bilirubin oxidase, granolocyte colony-stimulating factor, granolocyte macrophage colony-stimulating factor, macrophage colony-stimulating factor, neocarzinostatin, catalase, elastase, erythropoietin, interferon-α, interferon-β, interferon-γ, tumor necrosis factor-α, tumor necrosis factor-β, nerve growth factor, epidermal growth factor, ovalbumin, platelet derived growth factor, thrombomodulin, α antitrypsin, bone morphogenetic protein, cartilage derived factor, fibroblast growth factor, growth hormone, transforming growth factor-β, blood coagulation factor IX, protein C, protein S, insulin-like growth factor, calcitonin, somatostatin, tissue inhibitor of metalloproteinase, atrial natriuretic hormone, CD-4 protein cystatin, calpastatin, urinastatin or parathyroid hormone.*

*43. A protein compound according to claim 42, wherein W is a divalent radical of the formula* $(CH_2)_{12}$,$(CH_2)_{14}$, $(CH_2)_{16}$, $(CH_2)_{18}$ *or* $(CH_2)_{20}$.

*44. A protein compound according to claim 43, wherein said pharmacologically active protein is superoxide dismutase.*

*45. A protein compound according to claim 44, wherein W is* $(CH_2)_{12}$.

*46. The protein compound according to claim 45, wherein n is 3.6.*

*47. The protein compound according to claim 45, wherein n is 4.4.*

*48. The protein compound according to claim 45, wherein n is 5.4.*

*49. A protein compound according to claim 44, wherein W is* $(CH_2)_{16}$.

*50. The protein compound according to claim 49, wherein n is 2.0.*

*51. A protein compound according to claim 44, wherein W is* $(CH_2)_{18}$.

*52. The protein compound according to claim 51, wherein n is 2.0.*

*53. A protein compound according to claim 43, wherein said pharmacologically active protein is neocarzinostatin.*

*54. A protein compound according to claim 53, wherein W is* $(CH_2)_{14}$.

*55. The protein compound according to claim 54, having no free amino groups.*

*56. A protein compound according to claim 53, wherein W is* $(CH_2)_{16}$.

*57. The protein compound according to claim 56, having no free amino groups.*

*58. A process for preparing a protein compound having the formula*

$$(protein)(Z)_n$$

*wherein (protein) represents a pharmacologically active protein having n amino radicals each derivable from an amino group by removal of one of its hydrogen atoms, and (Z) is a radical of a long chain carboxylic acid having the formula*

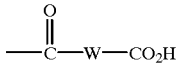

*wherein W is a divalent long chain hydrocarbon radical which is uninterrupted or interrupted by one or more groups each independently selected from the group consisting of an oxygen atom, a sulfur atom and a* —$N(R^1)$ *group wherein* $R^1$ *is lower alkyl, said radical W having from 8 to 28 principal chain atoms, each (Z) being derivable from a long-chain dicarboxylic acid* $HO_2C$—$W$—$CO_2H$ *by removal of a hydroxyl group from one of its carbonyl groups, each (Z) being bonded to one of said n amino radicals in said protein, n being an average of the number of amide bonds between (Z) and (protein) and being a number from 1 to 8, said process comprising reacting a compound of the formula:*

(II)

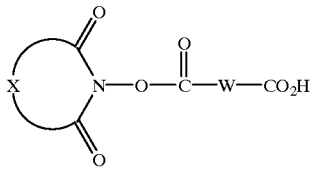

*or a salt thereof, wherein W is defined as above and*

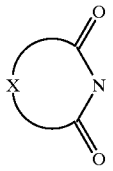

*is a radical of the formula*

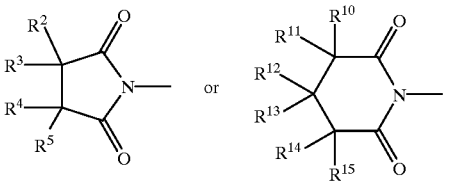

*wherein each of $R^2$, $R^3$, $R^4$ and $R^5$, which are the same or different, is a hydrogen atom; an alkyl radical; an aryl radical; an aralkyl radical; an —$SO_3H$ group; a radical of the formula —$OR^6$ wherein $R^6$ is selected from the group consisting of a hydrogen atom, an alkyl radical, an aryl radical, an aralkyl radical and an acyl radical; a radical of the formula —$NR^7R^8$ wherein each of $R^7$ and $R^8$, which are the same or different, is selected from the group consisting of an alkyl radical, an aryl radical, an aralkyl radical and an acyl radical; or a radical of the formula —$CO_2R^9$ wherein $R^9$ is selected from the group consisting of a hydrogen atom, an alkyl radical, an aryl radical and an aralkyl radical; or $R^2$, $R^3$, $R^4$ and $R^5$ in combination with the carbon atoms to which they bond, form a benzene, cyclohexane, cyclopentane, bicyclo[2.2.1]heptane, bicyclo[2.2.1]hepta-2-ene, 7-oxabicyclo[2.2.1]heptane or 7-oxabicyclo[2.2.1]hepta-2-ene ring system which is unsubstituted or substituted by —$SO_3H$, —$CO_2H$, —OH, F, Cl, Br, I, —$CH_3$ or —$OCH_3$; or $R^2$ and $R^3$, $R^4$ and $R^5$, or both, in combination, are a methylene or isopropylidene group; and each of $R^{10}$, $R^{11}$, $R^{12}$, $R^{13}$, $R^{14}$ and $R^{15}$, which are the same or different, is a hydrogen atom; an alkyl radical; an aryl radical; an aralkyl radical; an —$SO_3H$ group; a radical of the formula —$OR^6$ wherein $R^6$ is selected from the group consisting of a hydrogen atom, an alkyl radical; an aryl radical, an aralkyl radical and an acyl radical; a radical of the formula —$NR^7R^8$ wherein each of $R^7$ and $R^8$, which are the same or different, is selected from the group consisting of an alkyl radical, an aryl radical, an aralkyl radical and an aryl radical; or a radical of the formula —$CO_2R^9$ wherein $R^9$ is selected from the group consisting of a hydrogen atom, an alkyl radical, an aryl radical or an aralkyl radical;*

*with a pharmaceutically active protein defined as above in an aqueous solution at a pH maintained within the range of 6 to 10, at a reaction temperature of from about 3° to 50° C. which does not exceed the denaturation temperature of the protein;*

*followed by separating the resultant protein compound from the reaction medium.*

*59. A process according to claim 58, wherein the pharmacologically active protein starting material is asparaginase, arginase, interleukin-1, interleukin-2, interleukin-3, interleukin-4, interleukin-5, interleukin-6, interleukin-7, interleukin-8, urokinase, prourokinase, streptokinase, tissue plasminogen activator, β-glucosidase, β-glucuronidase, α-galactosidase, adenosine deaminase, uricase, superoxide dismutase, insulin, bilirubin oxidase, granolocyte colony-stimulating factor, granolocyte macrophage colony-stimulating factor, macrophage colony-stimulating factor, neocarzinostatin, catalase, elastase, erythropoietin, interferon-α, interferon-β, interferon-γ, tumor necrosis factor-α, tumor necrosis factor-β, nerve growth factor, epidermal growth factor, ovalbumin, platelet derived growth factor, thrombomodulin, α-antitrypsin, bone morphogenetic protein, cartilage derived factor, fibroblast growth factor, growth hormone, transforming growth factor-β, blood coagulation factor IX, protein C, protein S, insulin-like growth factor, calcitonin, somatostatin, tissue inhibitor of metalloproteinase, atrial natriuretic hormone, CD-4 protein, cystatin, calpastatin, urinastatin or parathyroid hormone.*

*60. A process according to claim 58, wherein the starting material of formula (II) is:*

*N-(13-carboxytridecanoyloxy)succinimide;*

*N-(15-carboxypentadecanoyloxy)succinimide;*

*N-(17-carboxyheptadecanoyloxy)succinimide;*

*N-(19-carboxynonadecanoyloxy)succinimide;*

*N-(21-carboxyheneicosanoyloxy)succinimide;*

*N-(15-carboxypentadecanoyloxy)phthalimide;*

*N-(15-carboxypentadecanoyloxy) tetramethylphthalimide;*

*N-(15-carboxypentadecanoyloxy)5-norbornene-2,3-dicarboximide;*

*N-(15-carboxypentadecanoyloxy)tartrimide;*

*N-(13-carboxytridecanoyloxy)sulfosuccinimide sodium salt;*

*N-(15-carboxypentadecanoyloxy)-3-isopropylsuccinimide;*

*N-(15-carboxypentadecanoyloxy) tetramethylsuccinimide;*

*N-(15-carboxypentadecanoyloxy)-3-benzylsuccinimide;*

*N-(15-carboxypentadecanoyloxy)itaconimide; or*

*N-(15-carboxypentadecanoyloxy)glutarimide.*

*61. A process according to claim 59, wherein the starting material of formula (II) is:*

*N-(13-carboxytridecanoyloxy)succinimide;*

*N-(15-carboxypentadecanoyloxy)succinimide;*

*N-(17-carboxyheptadecanoyloxy)succinimide;*

*N-(19-carboxynonadecanoyloxy)succinimide;*

*N-(21-carboxyheneicosanoyloxy)succinimide;*

*N-(15-carboxypentadecanoyloxy)phthalimide;*

*N-(15-carboxypentadecanoyloxy) tetramethylphthalimide;*

*N-(15-carboxypentadecanoyloxy)5-norbornene-2,3-dicarboximide;*

*N-(15-carboxypentadecanoyloxy)tartrimide;*

*N-(13-carboxytridecanoyloxy)sulfosuccinimide sodium salt;*

*N-(15-carboxypentadecanoyloxy)-3-isopropylsuccinimide;*

*N-(15-carboxypentadecanoyloxy) tetramethylsuccinimide;*

*N-(15-carboxypentadecanoyloxy)-3-benzylsuccinimide;*

*N-(15-carboxypentadecanoyloxy)itaconimide; or*

*N-(15-carboxypentadecanoyloxy)glutarimide.*

*62. A process according to claim 61, wherein the pharmacologically active protein starting material is superoxide dismutase and the starting material of formula (II) is N-(13-carboxytridecanoyloxy)succinimide.*

*63. A compound according to claim 61, wherein the pharmacologically active protein starting material is superoxide dismutase and the starting material of formula (II) is N-(17-carboxyheptadecanoyloxy)succinimide.*

*64. A process according to claim 61, wherein the pharmacologically active protein starting material is superoxide dismutase and the starting material of formula (II) is N-(19-carboxynonadecanoyloxy)succinimide.*

*65. A process according to claim 61, wherein the pharmacologically active protein starting material is neocarzinostatin and the starting material of formula (II) is N-(15-carboxypentadecanoyloxy)succinimide.*

*66. A process according to claim 61, wherein the pharmacologically active protein starting material is neocarzinostatin and the starting material of formula (II) is N-(17-carboxyheptadecanoyloxy)succinimide.*

* * * * *